United States Patent
Ben-David et al.

(10) Patent No.: US 11,744,589 B2
(45) Date of Patent: Sep. 5, 2023

(54) DEVICES AND METHODS FOR PROVIDING PASSAGE BETWEEN HEART CHAMBERS

(71) Applicant: V-Wave Ltd., Caesarea (IL)

(72) Inventors: Tamir Ben-David, Tel Aviv (IL); Neal Eigler, Agoura Hills, CA (US); Nir Nae, Binjamina (IL); Lior Rosen, Or Akiva (IL); Erez Rozenfeld, Shoham (IL); James S. Whiting, Los Angeles, CA (US)

(73) Assignee: V-Wave Ltd., Caesarea (IL)

( * ) Notice: Subject to any disclaimer, the term of this patent is extended or adjusted under 35 U.S.C. 154(b) by 110 days.

(21) Appl. No.: 16/963,139

(22) PCT Filed: Jan. 19, 2019

(86) PCT No.: PCT/IB2019/050452
§ 371 (c)(1),
(2) Date: Jul. 17, 2020

(87) PCT Pub. No.: WO2019/142152
PCT Pub. Date: Jul. 25, 2019

(65) Prior Publication Data
US 2021/0121179 A1      Apr. 29, 2021

Related U.S. Application Data

(60) Provisional application No. 62/619,748, filed on Jan. 20, 2018.

(51) Int. Cl.
*A61B 17/11* (2006.01)
*A61B 17/00* (2006.01)

(52) U.S. Cl.
CPC .......... *A61B 17/11* (2013.01); *A61B 17/0057* (2013.01); *A61B 2017/00022* (2013.01);
(Continued)

(58) Field of Classification Search
CPC .. A61B 2017/0022; A61B 2017/00243; A61B 2017/00592; A61B 2017/00606;
(Continued)

(56) References Cited

U.S. PATENT DOCUMENTS

| 3,852,334 A | 12/1974 | Dusza et al. |
| 3,874,388 A | 4/1975 | King et al. |

(Continued)

FOREIGN PATENT DOCUMENTS

| AU | 2003291117 B2 | 4/2009 |
| CA | 2378920 A1 | 2/2001 |

(Continued)

OTHER PUBLICATIONS

Ando et al., "Left ventricular decompression through a patent foramen ovale in a patient with hypertropic cardiomyopathy: A case report," Cardiovascular Ultrasound 2: 1-7 (2004).
(Continued)

*Primary Examiner* — Alexander J Orkin
(74) *Attorney, Agent, or Firm* — Eversheds Sutherland (US) LLP; Christopher C. Bolten; Albert K. Heng

(57) ABSTRACT

A device for providing a passage between a first and second heart chamber is provided. The device includes a middle region having first and second ends, a lumen extending therethrough having a longitudinal axis, a first end region coupled to the first end, and a second end region coupled to the second end. The first end region may be delivered in the first heart chamber in a compressed state and transitioned to a deployed state, the first end region being deformable such that portions of the first end region are expandable to different angles relative to the longitudinal axis. The second end region may be delivered in the second heart chamber in a compressed state and transitioned to a deployed state therein, the second end region being deformable such that
(Continued)

portions of the second end region are expandable to different angles relative to the longitudinal axis.

21 Claims, 18 Drawing Sheets

(52) U.S. Cl.
CPC ............... *A61B 2017/00084* (2013.01); *A61B 2017/00106* (2013.01); *A61B 2017/00243* (2013.01); *A61B 2017/00358* (2013.01); *A61B 2017/00592* (2013.01); *A61B 2017/00606* (2013.01); *A61B 2017/00623* (2013.01); *A61B 2017/1107* (2013.01); *A61B 2017/1139* (2013.01); *A61B 2562/0247* (2013.01)

(58) Field of Classification Search
CPC ........... A61B 2017/00623; A61B 2017/00139; A61B 17/0057; A61B 2017/1139; A61F 2/2418
See application file for complete search history.

(56) References Cited

U.S. PATENT DOCUMENTS

| | | | |
|---|---|---|---|
| 3,952,334 | A | 4/1976 | Bokros et al. |
| 4,364,395 | A | 12/1982 | Redmond et al. |
| 4,484,955 | A | 11/1984 | Hochstein |
| 4,601,309 | A | 7/1986 | Chang |
| 4,617,932 | A | 10/1986 | Kornberg |
| 4,662,355 | A | 5/1987 | Pieronne et al. |
| 4,665,906 | A | 5/1987 | Jervis |
| 4,705,507 | A | 11/1987 | Boyles |
| 4,836,204 | A | 6/1989 | Landymore et al. |
| 4,979,955 | A | 12/1990 | Smith |
| 4,988,339 | A | 1/1991 | Vadher |
| 4,995,857 | A | 2/1991 | Arnold |
| 5,035,702 | A * | 7/1991 | Taheri ................ A61B 17/11 606/153 |
| 5,035,706 | A | 7/1991 | Giantureo et al. |
| 5,037,427 | A | 8/1991 | Harada et al. |
| 5,089,005 | A | 2/1992 | Harada |
| 5,186,431 | A | 2/1993 | Tamari |
| 5,197,978 | A | 3/1993 | Hess |
| 5,234,447 | A * | 8/1993 | Kaster ................ A61B 17/11 606/151 |
| 5,267,940 | A | 12/1993 | Moulder |
| 5,290,227 | A | 3/1994 | Pasque |
| 5,312,341 | A | 5/1994 | Turi |
| 5,326,374 | A | 7/1994 | Ilbawi et al. |
| 5,332,402 | A | 7/1994 | Teitelbaum |
| 5,334,217 | A | 8/1994 | Das |
| 5,378,239 | A | 1/1995 | Termin et al. |
| 5,409,019 | A | 4/1995 | Wilk |
| 5,429,144 | A | 7/1995 | Wilk |
| 5,500,015 | A | 3/1996 | Deac |
| 5,531,759 | A | 7/1996 | Kensey et al. |
| 5,545,210 | A | 8/1996 | Hess et al. |
| 5,556,386 | A | 9/1996 | Todd |
| 5,578,008 | A | 11/1996 | Hara |
| 5,584,803 | A | 12/1996 | Stevens et al. |
| 5,597,377 | A | 1/1997 | Aldea |
| 5,645,559 | A | 7/1997 | Hachtman et al. |
| 5,655,548 | A | 8/1997 | Nelson et al. |
| 5,662,711 | A | 9/1997 | Douglas |
| 5,702,412 | A | 12/1997 | Popov et al. |
| 5,725,552 | A | 3/1998 | Kotula et al. |
| 5,741,324 | A | 4/1998 | Glastra |
| 5,749,880 | A | 5/1998 | Banas et al. |
| 5,779,716 | A | 7/1998 | Cano et al. |
| 5,795,307 | A | 8/1998 | Krueger |
| 5,810,836 | A | 9/1998 | Hussein et al. |
| 5,824,062 | A | 10/1998 | Patke et al. |
| 5,824,071 | A | 10/1998 | Nelson et al. |
| 5,846,261 | A | 12/1998 | Kotula et al. |
| 5,910,144 | A | 6/1999 | Hayashi |
| 5,916,193 | A | 6/1999 | Stevens et al. |
| 5,941,850 | A | 8/1999 | Shah et al. |
| 5,957,949 | A | 9/1999 | Leonhardt et al. |
| 5,990,379 | A | 11/1999 | Gregory |
| 6,027,518 | A | 2/2000 | Gaber |
| 6,039,755 | A | 3/2000 | Edwin et al. |
| 6,039,759 | A | 3/2000 | Carpentier et al. |
| 6,086,610 | A | 7/2000 | Duerig et al. |
| 6,111,520 | A | 8/2000 | Allen et al. |
| 6,117,159 | A | 9/2000 | Huebsch et al. |
| 6,120,534 | A | 9/2000 | Ruiz |
| 6,124,523 | A | 9/2000 | Banas et al. |
| 6,126,686 | A | 10/2000 | Badylak et al. |
| 6,165,188 | A | 12/2000 | Saadat et al. |
| 6,210,318 | B1 | 4/2001 | Lederman |
| 6,214,039 | B1 | 4/2001 | Banas et al. |
| 6,217,541 | B1 | 4/2001 | Yu |
| 6,221,096 | B1 | 4/2001 | Aiba et al. |
| 6,231,587 | B1 | 5/2001 | Makower |
| 6,242,762 | B1 | 6/2001 | Brown et al. |
| 6,245,099 | B1 | 6/2001 | Edwin et al. |
| 6,254,564 | B1 | 7/2001 | Wilk et al. |
| 6,260,552 | B1 | 7/2001 | Mortier et al. |
| 6,264,684 | B1 | 7/2001 | Banas et al. |
| 6,270,515 | B1 | 8/2001 | Linden et al. |
| 6,270,526 | B1 | 8/2001 | Cox |
| 6,277,078 | B1 | 8/2001 | Porat et al. |
| 6,278,379 | B1 | 8/2001 | Allen et al. |
| 6,290,728 | B1 | 9/2001 | Phelps et al. |
| 6,302,892 | B1 | 10/2001 | Wilk |
| 6,306,141 | B1 | 10/2001 | Jervis |
| 6,328,699 | B1 | 12/2001 | Eigler et al. |
| 6,344,022 | B1 | 2/2002 | Jarvik |
| 6,358,277 | B1 | 3/2002 | Duran |
| 6,391,036 | B1 | 5/2002 | Berg et al. |
| 6,398,803 | B1 | 6/2002 | Layne et al. |
| 6,406,422 | B1 | 6/2002 | Landesberg |
| 6,447,539 | B1 | 9/2002 | Nelson et al. |
| 6,451,051 | B2 | 9/2002 | Drasler et al. |
| 6,458,153 | B1 | 10/2002 | Bailey et al. |
| 6,468,303 | B1 | 10/2002 | Amplatz et al. |
| 6,475,136 | B1 | 11/2002 | Forsell |
| 6,478,776 | B1 | 11/2002 | Rosenman et al. |
| 6,485,507 | B1 | 11/2002 | Walak et al. |
| 6,488,702 | B1 | 12/2002 | Besselink |
| 6,491,705 | B2 | 12/2002 | Gifford et al. |
| 6,527,698 | B1 | 3/2003 | Kung et al. |
| 6,544,208 | B2 | 4/2003 | Ethier et al. |
| 6,547,814 | B2 | 4/2003 | Edwin et al. |
| 6,562,066 | B1 | 5/2003 | Martin |
| 6,572,652 | B2 | 6/2003 | Shaknovich |
| 6,579,314 | B1 | 6/2003 | Lombardi et al. |
| 6,589,198 | B1 | 7/2003 | Soltanpour et al. |
| 6,616,675 | B1 * | 9/2003 | Evard .................. A61B 1/3137 606/153 |
| 6,632,169 | B2 | 10/2003 | Korakianitis et al. |
| 6,638,303 | B1 | 10/2003 | Campbell |
| 6,641,610 | B2 | 11/2003 | Wolf et al. |
| 6,652,578 | B2 | 11/2003 | Bailey et al. |
| 6,685,664 | B2 | 2/2004 | Levin et al. |
| 6,712,836 | B1 | 3/2004 | Berg et al. |
| 6,740,115 | B2 | 5/2004 | Lombardi et al. |
| 6,758,858 | B2 | 7/2004 | McCrea et al. |
| 6,764,507 | B2 | 7/2004 | Shanley et al. |
| 6,770,087 | B2 | 8/2004 | Layne et al. |
| 6,797,217 | B2 | 9/2004 | McCrea et al. |
| 6,890,350 | B1 | 5/2005 | Walak et al. |
| 6,970,742 | B2 | 11/2005 | Mann et al. |
| 7,001,409 | B2 | 2/2006 | Amplatz |
| 7,004,966 | B2 | 2/2006 | Edwin et al. |
| 7,025,777 | B2 | 4/2006 | Moore |
| 7,060,150 | B2 | 6/2006 | Banas et al. |
| 7,083,640 | B2 | 8/2006 | Lombardi et al. |
| 7,115,095 | B2 | 10/2006 | Eigler et al. |
| 7,118,600 | B2 | 10/2006 | Dua et al. |
| 7,137,953 | B2 | 11/2006 | Eigler et al. |
| 7,147,604 | B1 | 12/2006 | Allen et al. |
| 7,149,587 | B2 | 12/2006 | Wardle et al. |

(56) References Cited

U.S. PATENT DOCUMENTS

| | | |
|---|---|---|
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,439,723 B2 | 10/2008 | Allen et al. |
| 7,468,071 B2 | 12/2008 | Edwin et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Hoang et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,251,740 B2 | 4/2019 | Eigler et al. |
| 10,251,750 B2 | 4/2019 | Eigler et al. |
| 10,265,169 B2 | 4/2019 | Desrosiers et al. |
| 10,299,687 B2 | 5/2019 | Nabutovsky et al. |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,109,988 B2 | 9/2021 | Rosen et al. |
| 11,234,702 B1 | 2/2022 | Eigler et al. |
| 11,253,353 B2 | 2/2022 | Levi et al. |
| 11,291,807 B2 | 4/2022 | Eigler et al. |
| 11,304,831 B2 | 4/2022 | Nae et al. |
| 2001/0021872 A1* | 9/2001 | Bailey ........................ A61F 2/07 |
| | | 623/1.24 |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1* | 3/2003 | Weadock ............... A61B 17/11 |
| | | 606/219 |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |

(56) References Cited

U.S. PATENT DOCUMENTS

| | | | |
|---|---|---|---|
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0165344 A1 | 7/2005 | Dobak |
| 2005/0182486 A1 | 8/2005 | Gabbay |
| 2005/0267524 A1* | 12/2005 | Chanduszko | A61B 17/0057 606/213 |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1* | 12/2005 | Chanduszko | A61B 17/0057 623/11.11 |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0111660 A1 | 5/2006 | Wolf et al. |
| 2006/0116710 A1 | 6/2006 | Corcoran et al. |
| 2006/0122522 A1* | 6/2006 | Chavan | A61B 5/6862 600/505 |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1 | 8/2007 | De Juan et al. |
| 2007/0213813 A1 | 9/2007 | Von Segesser et al. |
| 2007/0249985 A1* | 10/2007 | Brenneman | A61B 17/083 604/890.1 |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1* | 7/2008 | Brenneman | A61B 17/11 600/509 |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |

(56) References Cited

U.S. PATENT DOCUMENTS

| | | |
|---|---|---|
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0005810 A1* | 1/2015 | Center ................ A61F 2/01 606/200 |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1* | 4/2015 | Sherman ........... A61B 17/0057 606/213 |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0313599 A1* | 11/2015 | Johnson ................ A61B 17/11 606/191 |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1 | 3/2017 | Cooper et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0091438 A1 | 3/2019 | Higgins et al. |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2022/0211361 A1 | 7/2022 | Rolando et al. |
| 2022/0304803 A1 | 9/2022 | Guyenot et al. |

FOREIGN PATENT DOCUMENTS

| | | |
|---|---|---|
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-1997/27898 A1 | 8/1997 |
| WO | WO-1999/60941 A1 | 12/1999 |
| WO | WO-2000/44311 A2 | 8/2000 |
| WO | WO-0050100 A1 | 8/2000 |
| WO | WO-2001/10314 A2 | 2/2001 |
| WO | WO-0126585 A1 | 4/2001 |
| WO | WO-2002/026281 A1 | 4/2002 |
| WO | WO-2002/071974 A2 | 9/2002 |
| WO | WO-02087473 A1 | 11/2002 |
| WO | WO-2003/053495 A2 | 7/2003 |
| WO | WO-2005/027752 A1 | 3/2005 |
| WO | WO-2005/074367 A1 | 8/2005 |
| WO | WO-2006/127765 A1 | 11/2006 |
| WO | WO-2007/083288 A2 | 7/2007 |
| WO | WO-2008/055301 A1 | 5/2008 |
| WO | WO-2008070797 A2 | 6/2008 |
| WO | WO-2009/029261 A1 | 3/2009 |
| WO | WO-2010/128501 A1 | 11/2010 |
| WO | WO-2010/129089 A2 | 11/2010 |
| WO | WO-2010139771 A2 | 12/2010 |
| WO | WO-2011/062858 A1 | 5/2011 |
| WO | WO-2013/096965 A1 | 6/2013 |
| WO | WO-2016/178171 A1 | 11/2016 |
| WO | WO-2017/031235 A1 | 2/2017 |
| WO | WO-2017/118920 A1 | 7/2017 |
| WO | WO-2018/158747 A1 | 9/2018 |
| WO | WO-2019/015617 A1 | 1/2019 |
| WO | WO-2019/085841 A1 | 5/2019 |
| WO | WO-2019/109013 A1 | 6/2019 |
| WO | WO-2019/142152 A1 | 7/2019 |
| WO | WO-2019/179447 A1 | 9/2019 |
| WO | WO-2019218072 A1 | 11/2019 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |
| WO | WO-2022046921 A1 | 3/2022 |

(56) References Cited

FOREIGN PATENT DOCUMENTS

| WO | WO-2022076601 A1 | 4/2022 |
|---|---|---|
| WO | WO-2022091018 A1 | 5/2022 |
| WO | WO-2022091019 A1 | 5/2022 |

OTHER PUBLICATIONS

Atrium Advanta V12, Balloon Expandable Covered Stent, Improving Patient Outcomes with An Endovascular Approach, Brochure—8 pages, Getinge (2017).
Boehm, et al., Balloon Atrial Septostomy: History and Technique, Images Paeditr. Cardiol., 8(1):8-14 (2006).
Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Bristow et al., Improvement in cardiac myocite function by biological effects of medical therapy: a new concept in the treatment of heart failure, European Heart Journal 16 (Suppl.F): 20-31 (1995).
Case et al., "Relief of High Left-Atrial Pressure in Left-Ventricular Failure," Lancet, pp. 841-842 (Oct. 14, 1964).
Coats et al., "Controlled trial of physical training in chronic heart failure: Exercise performance, hemodynamics, ventilation and autonomic function," Circulation 85:2119-2131 (1992).
Drexel, et al., The Effects of Cold Work and Heat Treatment on the Properties of Nitinol Wire, Proceedings of the International Conference on Shape Memory and Superelastic Technologies, May 7-11, 2006, Pacific Grove, California, USA (pp. 447-454).
Eigler, et al., Implantation and Recovery of Temporary Metallic Stents in Canine Coronary Arteries, JACC, 22(4):1207-1213 (1993).
Ennezat et al., An unusual case of low-flow, low-gradient severe aortic stenosis: Left-to-right shunt due to atrial septal defect, Cardiology 113(2): 146-148 (2009).
Ewert et al., "Acute left heart failure after interventional occlusion of an atrial septal defect," Z Kardiol. 90(5): 362-366 (May 2001).
Ewert et al., Masked Left Ventricular Restriction in Elderly Patients With Atrial Septal Defects: A Contraindication for Closure?, Catheterization and Cardiovascular Interventions 52: 177-180 (2001).
Extended EP Search Report dated Sep. 19, 2016 in EP Patent Application Serial No. 16170281.6.
Extended European Search Report dated Jan. 8, 2015 in EP Patent Appl. No. 10772089.8.
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Conginit. Heart Dis. 31(1) 47-53 (Jan. 2008).
Gewillig et al., "Creation with a stent of an unrestrictive lasting atrial communication," Cardio. Young 12(4): 404-407 (2002).
International Search Report & Written Opinion dated May 29, 2018 in Int'l PCT Patent Appl. Serial No. PCTIB2018/051355.
International Search Report for PCT/IL2005/000131, 3 pages (dated Apr. 7, 2008).
International Search Report for PCT/IL2010/000354 dated Aug. 25, 2010 (1 pg).
Int'l Search Report & Written Opinion dated Feb. 16, 2015 in Int'l PCT Patent Appl. Serial No. PCT/IB2014/001771.
International Search Report & Written Opinion dated Feb. 7, 2020 in Int'l PCT Patent Appl. Serial No. PCT/IB2019/060257.
Partial International Search Report dated Jun. 18, 2020 in Int'l PCT Patent Appl. Serial No. PCT/IB2020/053118.
International Search Report & Written Opinion dated Jul. 14, 2020 in Int'l PCT Patent Appl. Serial No. PCT/IB2020/053832.
International Search Report & Written Opinion dated May 13, 2019 in Int'l PCT Patent Appl. Serial No. PCT/IB2019/050452.
International Search Report & Written Opinion dated Jul. 20, 2020 in Int'l PCT Patent Appl. Serial No. PCT/IB2020/054699.

Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., Bidirectional Shunt Through a Residual Atrial Septal Defect After Percutaneous Transvenous Mitral Commissurotomy, Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of 'Chamber'," O-line Dictionary 2004, Abstract.
Park, et al., Blade Atrial Septostomy: Collaborative Study, Circulation, 66(2):258-266 (1982).
Partial International Search dated Aug. 17, 2017 in Int'l PCT Patent Appl. Serial No. PCT/IB2017/053188.
Partial Supplemental European Search Report dated Dec. 11, 2018 in EP Patent Appl. Serial No. 1678939.6.
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31 (4):348-353 (2008).
Schubert et al., Left Ventricular Conditioning in the Elderly Patient to Prevent Congestive Heart Failure After Transcatheter Closure of the Atrial Septal Defect, Catheterization and Cardiovascular Interventions,64(3): 333-337 (2005).
Stormer et al., Comparative Study of n vitro Flow Characteristics Between a Human Aortic Valve and a Designed Aortic Valve and Six Corresponding Types of Prosthetic Heart Valves, European Surgical Research 8(2): 117-131 (1976).
Stumper et al., "Modified technique of stent fenestration of the atrial septum," Heart 89: 1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).
U.S. Appl. No. 09/839,643 / U.S. Pat. No. 8,091,556, filed Apr. 20, 2001 / Jan. 10, 2012.
U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.

(56) References Cited

OTHER PUBLICATIONS

U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752, filed Oct. 31, 2017.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.
U.S. Appl. No. 15/668,622 / U.S. Pat. No. 10,463,490, filed Aug. 3, 2017 / Nov. 5, 2019.
U.S. Appl. No. 15/798,250, filed Oct. 30, 2017.
U.S. Appl. No. 16/130,978 / U.S. Pat. No. 10,251,740, filed Sep. 13, 2018 / Apr. 9, 2019.
U.S. Appl. No. 16/130,988, filed Sep. 13, 2018.
U.S. Appl. No. 16/205,213, filed Nov. 29, 2018.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/686,013, filed Nov. 15, 2019.
U.S. Appl. No. 16/672,420, filed Nov. 1, 2019.
U.S. Appl. No. 16/866,377, filed May 4, 2020.
U.S. Appl. No. 16/875,652, filed May 15, 2020.
U.S. Appl. No. 16/876,640, filed May 18, 2020.
U.S. Appl. No. 16/878,228, filed May 19, 2020.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the Champion randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Article 34 Amendments dated May 28, 2013 in Int'l PCT Patent Appl. Serial No. PCT/IB2012/001859.
Article 34 Amendments dated Nov. 27, 2012 in Int'l PCT Patent Appl. Serial No. PCT/IL2011/000958.
Ataya et al., "A Review of Targeted Pulmonary Arterial Hypertension-Specific Pharmacotherapy," J. Clin. Med., 5(12):114 (2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," Chest, 156(6):1176-1186 (2019).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Davies, et al., "Reduced Contraction and Altered Frequency Response of Isolated Ventricular Myocytes From Patients With Heart Failure, Circulation," 92: 2540-2549 (1995).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).

(56) References Cited

OTHER PUBLICATIONS

Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eshaghian et al., "Relation of Loop Diuretic Dose to Mortality in Advanced Heart Failure," Am J Cardiol., 97:1759-1764 (2006).
Extended European Search Report dated Mar. 29, 2019 in EP Patent Appl. Serial No. EP16789391.
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561.
International Search Report & Written Opinion dated Feb. 6, 2013 in Int'l PCT Patent Appl. No. PCT/IB2012/001859, 12 pages.
International Search Report & Written Opinion dated Feb. 9, 2022 in Int'l PCT Patent Appl. Serial No. PCT/IB2021/060473.
International Search Report & Written Opinion dated Jul. 23, 2021 in Int'l PCT Patent Appl. Serial No. PCT/IB2021/053594.
International Search Report & Written Opinion dated Aug. 28, 2012 in Int'l PCT Patent Appl. No. PCT/IL2011/000958.
International Search Report & Written Opinion dated Sep. 21, 2020 in Int'l PCT Patent Appl. Serial No. PCT/IB2020/054306.
International Search Report & Written Opinion dated Oct. 11, 2017 in Int'l PCT Patent Appl. Serial No. PCT/IB2017/053188.
International Search Report & Written Opinion dated Oct. 26, 2007 in Int'l PCT Patent Appl. Serial No. PCT/IB07/50234.
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:867-77 (2009).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
Macdonald et al., "Emboli Enter Penetrating Arteries of Monkey Brain in Relation to Their Size," Stroke, 26:1247-1251 (1995).

(56) References Cited

OTHER PUBLICATIONS

Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21 (6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1-113507-5 (2014).
Nagaraju et al., "A 400µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi: 10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).

Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin .2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2.
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).

(56) References Cited

OTHER PUBLICATIONS

Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Wang et al., "Tire Pressure Monitoring System and Wireless Passive Surface Acoustic Wave Sensor," Appl Meeh Mater., 536(537):333-337 (2014).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Borlaug, et al., Latent Pulmonary Vascular Disease May Alter The Response to Therapeutic Atrial Shunt Device in Heart Failure, Circulation (Mar. 2022).
Flachskampf, et al., Influence of Orifice Geometry and Flow Rate on Effective Valve Area: An In Vitro Study, Journal of the American College of Cardiology, 15(5):1173-1180 (Apr. 1990).
International Search Report & Written Opinion dated May 17, 2022 in Int'l PCT Patent Appl. Serial No. PCT/IB2022/051177.
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Shah, et al., Atrial Shunt Device For Heart Failure With Preserved And Mildly Reduced Ejection Fraction (Reduce LAP-HF II): A Randomised, Multicentre, Blinded, Sham-Controlled Trial, The Lancet, 399(10330):1130-1140 (Mar. 2022).

\* cited by examiner

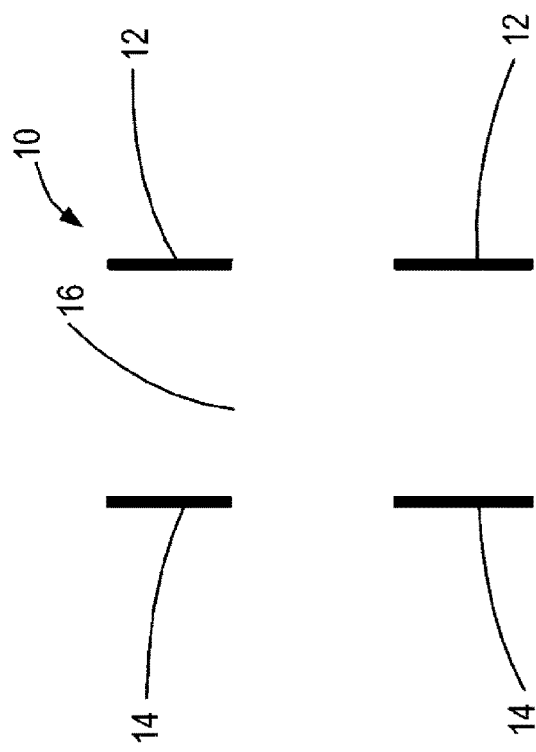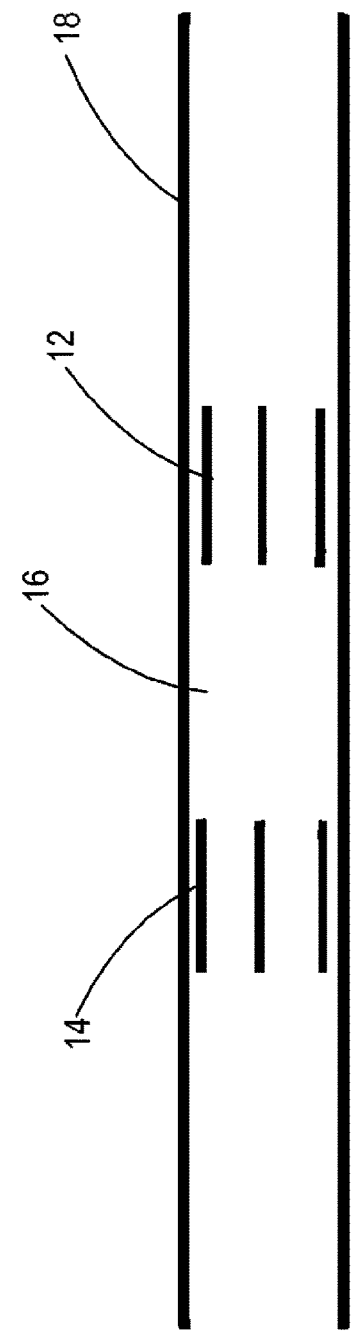

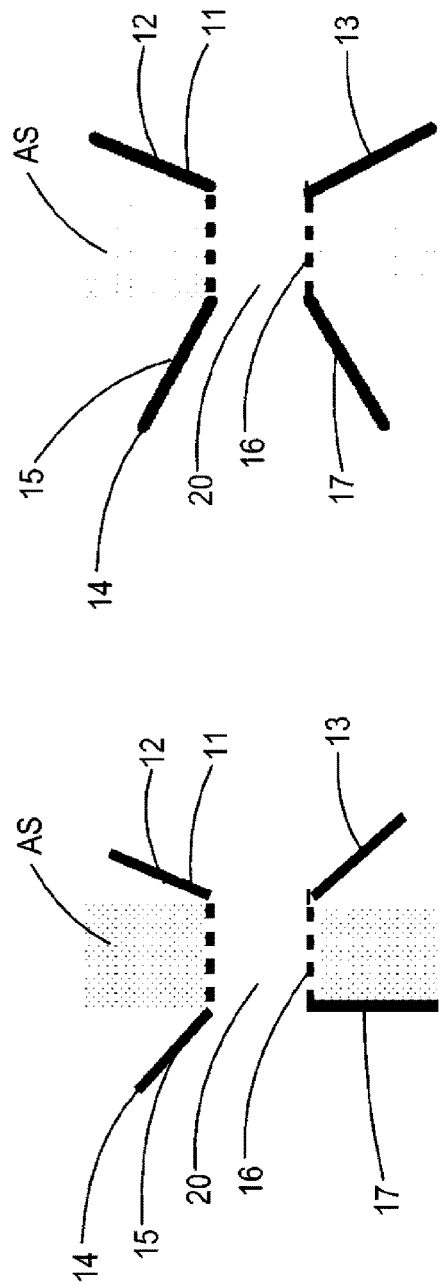
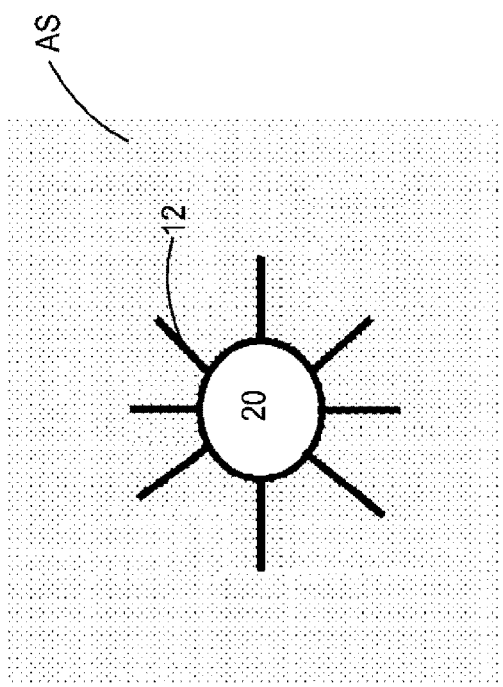

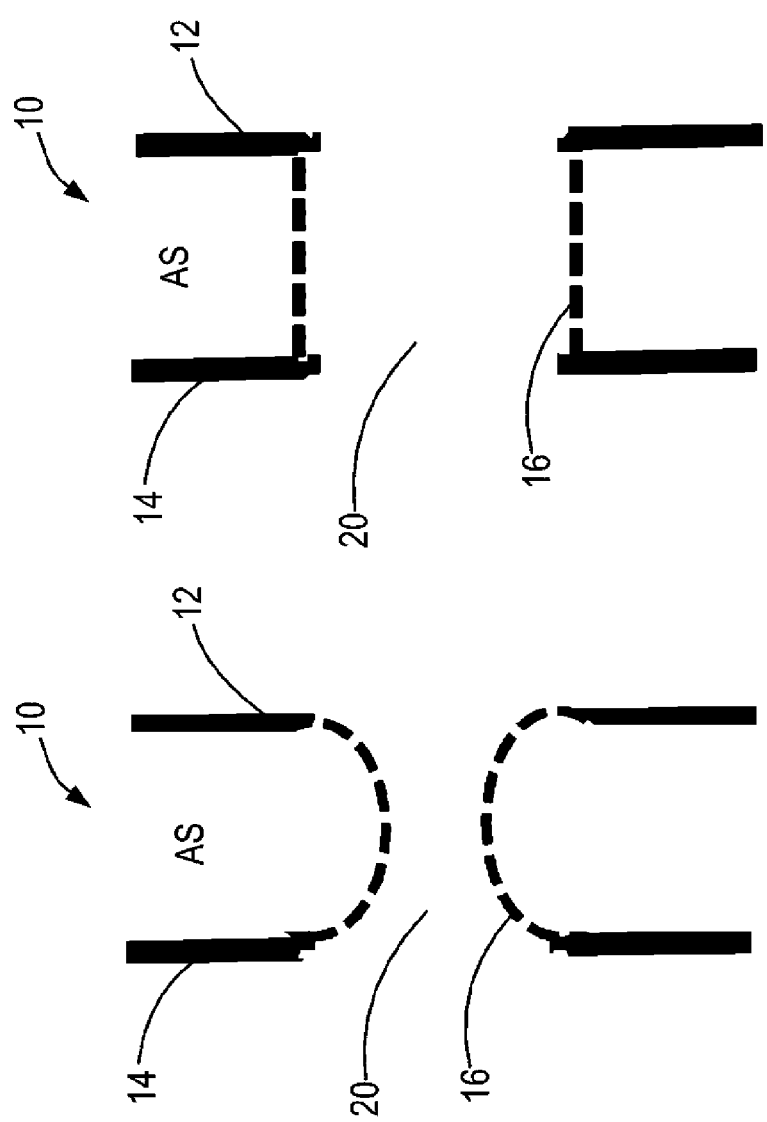

DEVICES AND METHODS FOR PROVIDING PASSAGE BETWEEN HEART CHAMBERS

CROSS-REFERENCE TO RELATED APPLICATIONS

This application is a national phase application under 35 U.S.C. § 371 of PCT/IB2019/050452, filed Jan. 19, 2019, which claims priority to U.S. Patent Provisional Application Ser. No. 62/619,748, filed Jan. 20, 2018, the entire contents of each of which are incorporated by reference herein.

FIELD OF THE INVENTION

This application generally relates to percutaneously placed implants and methods for providing a passage between body cavities, e.g., heart chambers, to address pathologies such as heart failure ("HF"), myocardial infarction ("MI") and pulmonary arterial hypertension ("PAH"), and to provide access to a surgeon's tool between the heart chambers.

BACKGROUND OF THE INVENTION

For a number of medical conditions, there is benefit in creating and/or maintaining a passage between two body cavities. Such a passage is typically used in catheterization procedures where the catheter is delivered through a patient's vasculature. In some catheterization procedures, there is a benefit in moving from one cavity to another cavity by creating a passage. For example, such a passage may be formed between the right side of the heart and the left side of the heart, e.g., between the right atrium toward the left atrium, where clinical procedures are done on the left side of the heart using an entry from the right side of the heart. Such clinical procedures include, e.g., AV nodal ablation in the left atrium or left ventricle and mitral valve repair activities.

In addition, a passage may be created and maintained in a heart wall between two heart chambers for housing a shunt for redistributing blood from one heart chamber to another to address pathologies such as HF, MI, and PAH. Heart failure is the physiological state in which cardiac output is insufficient to meet the needs of the body or to do so only at a higher filling pressure. There are many underlying causes of HF, including myocardial infarction, coronary artery disease, valvular disease, hypertension, and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts normally, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, beta blockers, and mineralocorticoid antagonists. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, assist devices such as mechanical pumps are used to reduce the load on the heart by performing all or part of the pumping function normally done by the heart. Chronic left ventricular assist devices ("LVAD"), and cardiac transplantation, often are used as measures of last resort. However, such assist devices typically are intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of HF or the reduction of left atrial pressure.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Shunt flow is generally governed by the pressure gradient between the atria and the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is placed from an entrance site in the femoral vein, across the interatrial septum in the region of fossa ovalis ("FO"), which is the central and thinnest region of the interatrial septum. The FO in adults is typically 15-20 mm in its major axis dimension and ≤3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital secundum atrial septal defect ("ASD") would be located.

U.S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

In addition, following implantation of a shunt device within a heart wall, tissue ingrowth including an endothelial layer or neointima layer typically forms on the device, thereby inhibiting thrombogenicity of the shunt device, and narrowing the size of the passage through the device. U.S. Patent Publication No. 2013/0178784 to McNamara describes an adjustable pressure relief shunt that may be expanded, e.g., via an inflation balloon. McNamara describes that the tubular body of the shunt may be plastically deformable and that the size of the shunt may be repeatedly adjusted responsive to measurements of the patient's physiological parameters. McNamara does not describe adjusting the size of the shunt to accommodate specifically sized clinical procedure tools used by the surgeon.

It would therefore be desirable to provide device and methods for adjusting the size of a passage through a device in situ to responsive to the clinical procedures performed by the surgeon.

In addition, it would further be desirable to provide device and methods for adjusting the cross-sectional area at the inlet and outlet ends of the device in situ.

It further may be beneficial to create passages between the venous blood vessels and the arterial blood vessels, between the venous blood vessels and the heart chambers, or between arterial blood vessels and the heart chambers. Following the catheterization procedure such passages are normally left open or sealed by special sealing devices such as an atrial septal occluder.

SUMMARY OF THE INVENTION

In view of the foregoing drawbacks of previously-known shunt devices, an adjustable passage device constructed in accordance with the principles of the present invention provides a more durable configuration that maintains luminal patency for extended periods of time. The inventive adjustable passage devices further enable particular selection of desired passage diameters for permitting various sized catheterization tools therethrough, as well as inlet and outlet diameters and angles so as to conform to a variety of tissue geometries between adjacent body cavities, thereby securely anchoring the passage device within the tissue.

In accordance with one aspect of the present invention, a device for providing a passage between a first heart chamber and a second heart chamber is provided. The device includes a middle region having first and second ends, a lumen extending therethrough, and a longitudinal axis aligned with the lumen, a first end region coupled to the first end, and a second end region coupled to the second end. The first end region may be delivered in the first heart chamber in a compressed delivery state and transitioned to a deployed state therein, the first end region being selectively deformable such that selected portions of the first end region are expandable to different angles relative to the longitudinal axis. In addition, the second end region may be delivered in the second heart chamber in a compressed delivery state and transitioned to a deployed state therein, the second end region being selectively deformable such that selected portions of the second end region are expandable to different angles relative to the longitudinal axis. At least one of the selected portions of the first or second end regions are expandable to an angle between zero and 90 degrees relative to the longitudinal axis of the device. The first and second end regions are constructed to anchor the middle region within a heart wall between the first heart chamber and the second heart chamber when in the expanded deployed state.

The first and second end region may be formed of a plastically deformable material. In addition, the first and second end regions may be transitionable from the compressed delivery state to the expanded deployed state via different sized non-compliant balloons. In accordance with one aspect of the present invention, the first and second end regions include a plurality of support arms extending from the middle region, the plurality of support arms coupled circumferentially along outer edges of the middle region of the device. In accordance with another aspect of the present invention, the first and second end regions are integrally formed with the middle region, such that the first and second end regions and the middle region are formed of a plurality of longitudinal struts interconnected by a plurality of circumferential sinusoidal struts. Accordingly, at least one of the first or second end regions has at least one of a conical or bell shape.

Moreover, the middle region is adjustable from a first state having a first diameter to a second state having a second diameter different from the first diameter. For example, the middle region may be formed of a plastically deformable material and/or an expandable mesh tube. The second diameter may be larger than the first diameter, or it may be smaller than the first diameter. The middle region may be adjusted from the first state to the larger second state via an inflatable balloon catheter. For example, the balloon catheter may be a dog bone shape or a quadrilateral dog bone shape. In addition, the passage device may include one or more sensors for measuring blood flow through the passage between the first heart chamber and the second heart chamber, such that the middle region may be adjusted from the first state to the second state responsive to the measured blood flow.

The middle region of the device further may be coupled to a medical device to thereby anchor the medical device within the heart wall between the first heart chamber and the second heart chamber. For example, the medical device may be at least one of a septal occluder, an open atrial septal shunt, a valved atrial septal shunt, a left atrial blood pressure sensor, or a blood pump. In accordance with one aspect of the present invention, the first heart chamber is a left atrium and the second heart chamber is a right atrium, such that the device permits blood flow through the passage between the left atrium and the right atrium.

In accordance with another aspect of the present invention, a method for providing a passage between a first heart chamber and a second heart chamber is provided. The method includes selecting a device having a first end region, a second end region, and a middle region extending between the first and second end regions, the middle region having a lumen for providing the passage between the first heart chamber and the second heart chamber. The method further includes delivering the device in a compressed delivery state within a heart wall of a patient such that the first end region is disposed within the first heart chamber, the second end region is disposed within the second heart chamber, and the middle region is positioned within the heart wall. In addition, the method includes expanding the first end region from the compressed delivery state to an expanded deployed state such that selected portions of the first end region have different angles relative to a longitudinal axis of the device, and expanding the second end region from the compressed delivery state to an expanded deployed state such that selected portions of the second end region have different angles relative to a longitudinal axis of the device, thereby providing the passage through the lumen of the middle region between the first heart chamber and the second heart chamber. Further, the method may include adjusting an angle of the first end region relative to the longitudinal axis of the device, and adjusting an angle of the second end region relative to the longitudinal axis of the device to achieve a predetermined flowrate across the passage between the first heart chamber and the second heart chamber.

BRIEF DESCRIPTION OF DRAWINGS

FIGS. 1A and 1B are cross-sectional views of an exemplary passage device in an expanded deployed state and a compressed delivery state, respectively, constructed in accordance with the principles of the present invention.

FIGS. 2A to 2D illustrate various expanded deployed configurations of the device of FIG. 1A disposed within a tissue between two heart chambers in accordance with the principles of the present invention.

FIG. 3 is a front view of the device of FIG. 1A disposed within a heart wall between two heart chambers.

FIGS. 9A to 9C are cross-sectional views of an embodiment of a passage device wherein the passage through the device is adjusted in situ in accordance with the principles of the present invention.

DETAILED DESCRIPTION OF THE PREFERRED EMBODIMENTS

Figure 2B:
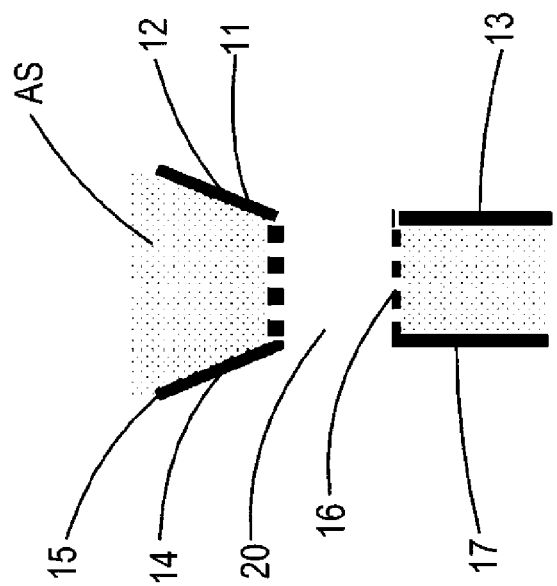

Devices are provided for providing a passage between adjacent body cavities, e.g., hearth chambers, within a patient. The diameter of the passage through the device may be adjusted accordingly responsive to the needs of the clinical procedure through the passage. In addition, the angles and cross-sectional areas of the proximal and distal end regions of the device may be independently selected to secure the device within the tissue, e.g., heart wall, and to selectively control the flowrate through the device responsive to the pressure gradient across the device. Further, the device may be designed to anchor an additional medical device within the heart wall, such as a septal occluder, an open atrial septal shunt, a valved atrial septal shunt, a left atrial blood pressure sensor, or a blood pump.

Referring now to FIGS. 1A and 1B, an exemplary passage device is provided. Passage device 10 includes first end region 12, second end region 14, and middle region 16 extending between first end region 12 and second end region 14. First end region 12 and second end region 14 may be formed of an expandable material such that first end region 12 and second end region 14 are transitionable between an expanded deployed state as shown in FIG. 1A, and a compressed delivery state as shown in FIG. 1B. As illustrated in FIG. 1B, passage device 10 may be disposed within sheath 18 in the compressed delivery state for percutaneously delivery to the target site.

Middle region 16 of passage device 10 may be formed from a mesh tube of a material having plastic properties, e.g., Cobalt Chromium. Accordingly, middle region 10 also may be transitionable between a compressed delivery state and an expanded deployed state. For example, Cobalt Chromium mesh tube may first undergo elastic deformation subject to stress that is lower than its yield strength prior to plastic deformation. Alternatively, the Cobalt Chromium mesh tube may receive a designated heat treatment prior to plastic deformation to optimize performance for its specific application and/or desired geometry. Upon delivery and deployment of passage device 10 at the target tissue, e.g., heart wall, the diameter of the lumen of middle region 16 may be further adjusted to a desired size. Specifically, the plastically deformable material of middle region 16 may be expanded to a desired size such that the plastically deformable material maintains the desired size upon removal of the expansion force applied to middle region 16. For example, different catheterization procedures may require tools of various sizes, and thus, middle region 16 of passage device 10 may be adjusted to have a diameter sufficient to permit a desired tool to pass therethrough. In addition, middle region 16 may be compressed to a smaller desired size such that the plastically deformable material maintains the smaller desired size upon removal of the compression force applied to middle region 16, e.g., via a snare.

Figure 2A:
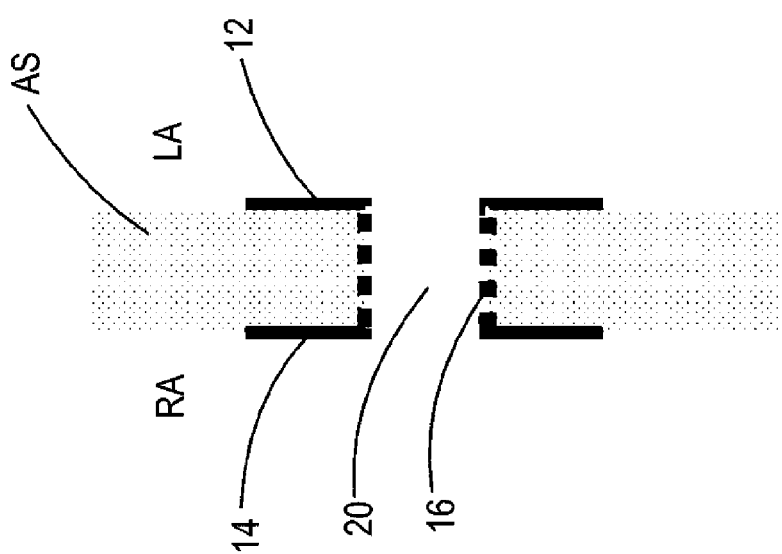

Referring now to FIGS. 2A to 2D, passage device 10 may be deployed within a heart wall of the patient, e.g., atrial septum AS. Accordingly, as shown in FIG. 2A, when middle region 16 is positioned within an opening in atrial septum AS, first end portion 12 of passage device 10 may be disposed within left atrium LA and second end portion 14 of passage device 10 may be disposed within right atrium RA, thereby providing passage 20 through middle region 16 in fluid communication with left atrium LA and right atrium RA. Moreover, as shown in FIG. 2A, first end region 12 and second end region 14 may be expanded such that they each extend into their respective atria at an angle of 90 degrees relative to the longitudinal axis of passage device 10. Accordingly, first end region 12 and second end region 14 may extend parallel along the wall of the atrial septum AS. This permits first end region 12 and second end region 14 to anchor middle region 16 within atrial septum AS.

As shown in FIG. 2B, first portion 11 of first end region 12 may be expanded such that it extends into the left atrium at an angle between 45 degrees and 90 degrees relative to the longitudinal axis of passage device 10, whereas second portion 13 of first end region 12 is expanded such that it extends into the left atrium at an angle of 90 degrees relative to the longitudinal axis of passage device 10, to thereby conform to the shape of atrial septum AS from within the left atrium as depicted in FIG. 2B. Similarly, first portion 15 of second end region 14 may be expanded such that it extends into the right atrium at an angle between 45 degrees and 90 degrees relative to the longitudinal axis of passage device 10, whereas second portion 17 of second end region 14 is expanded such that it extends into the right atrium at an angle of 90 degrees relative to the longitudinal axis of passage device 10, to thereby conform to the shape of atrial septum AS from within the right atrium as depicted in FIG. 2B. These expansions may be carried out via various sized balloon catheters, and/or a balloon catheter having various expandable portions, each independently inflatable to a desired inflation size. As will be understood by a person having ordinary skill in the art, first portion 11 and second portion 13 may be expanded such that they extend into the left atrium at any angle relative to the longitudinal axis of passage device 10 as may be required to anchor passage device 10 within atrial septum AS. For example, first portion 11 and second portion 13 may be expanded such that they extend into the left atrium at an angle between zero and 90 degrees, or even greater than 90 degrees.

Referring now to FIG. 2C, first end region 12 is selectively deformable such that selected portions of first end region 12 are expandable to different angles relative to the longitudinal axis of passage device 10, and first end region 12 is selectively deformable such that selected portions of first end region 12 are expandable to different angles relative to the longitudinal axis of passage device 10. For example, first portion 11 of first end region 12 may be expanded such that it extends into the left atrium at an angle between 45 degrees and 90 degrees relative to the longitudinal axis of passage device 10, whereas second portion 13 of first end region 12 is expanded such that it extends into the left atrium at an angle of 45 degrees relative to the longitudinal axis of passage device 10. Further, first portion 15 of second end region 14 may be expanded such that it extends into the right atrium at an angle of 45 degrees relative to the longitudinal axis of passage device 10, whereas second portion 17 of second end region 14 is expanded such that it extends into the right atrium at an angle of 90 degrees relative to the longitudinal axis of passage device 10. The selective expansion of selected portions of first end region 12 and second end region 14 may be carried out via different sized non-compliant balloons, and/or a balloon catheter having various expandable portions, each independently inflatable to a desired inflation size.

Referring now to FIG. 2D, first end region 12 may be transitioned from a contracted delivery state to an expanded deployed state in which first end region 12 extends into the left atrium at a first angle relative to a longitudinal axis of passage device 10, whereas second end region 14 is transitioned from a contracted delivery state to an expanded deployed state in which second end region 14 extends into the right atrium at a second angle relative to the longitudinal axis of passage device 10 that is different from the first angle of first end region 12. Therefore, the angles of inlet, e.g., first end region 12, and the outlet, e.g., second end region 14, of passage device 10, may be selected to precisely control and optimize the flowrate of blood through passage 20 of passage device 10 when passage device 10 is utilized as a shunt between the left and right atria, thereby changing the coefficient of discharge ("CD") of passage device 10, i.e., the ratio between the effective orifice area to the true orifice area. For example, if first end region 12 is expanded to 90 degrees relative to the longitudinal axis of passage device 10 to match the plane of the atrial septum, the CD is about 0.65, while if first end region 12 is expanded to 45 degrees relative to the longitudinal axis of passage device 10, the CD may be around 0.9. In addition, the inlet and outlet angles may be selected to control and optimize flow dynamics with respect to minimization of turbulence and flow stagnation across passage device 10.

As shown in FIG. 2D, first portion 11 and second portion 13 of first end region 12 may be expanded such that they extend into the left atrium at an angle between 45 degrees and 90 degrees relative to the longitudinal axis of passage device 10, whereas first portion 15 and second portion 17 of second end region 14 are expanded such that they extend into the right atrium at an angle between zero and 45 degrees relative to the longitudinal axis of passage device 10. The expansion of first end region 12 and second end region 14 may be carried out via different sized non-compliant balloons, and/or a balloon catheter having various expandable portions, each independently inflatable to a desired inflation size.

Figure 4B:
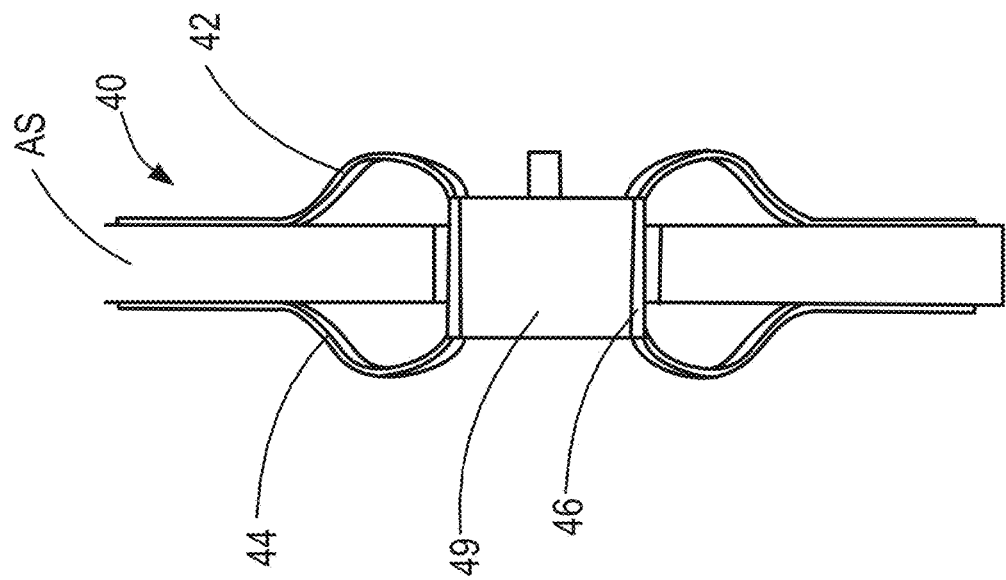
FIG. 4B illustrates the device of FIG. 4A having a sensor device disposed therein.
Figure 4A:
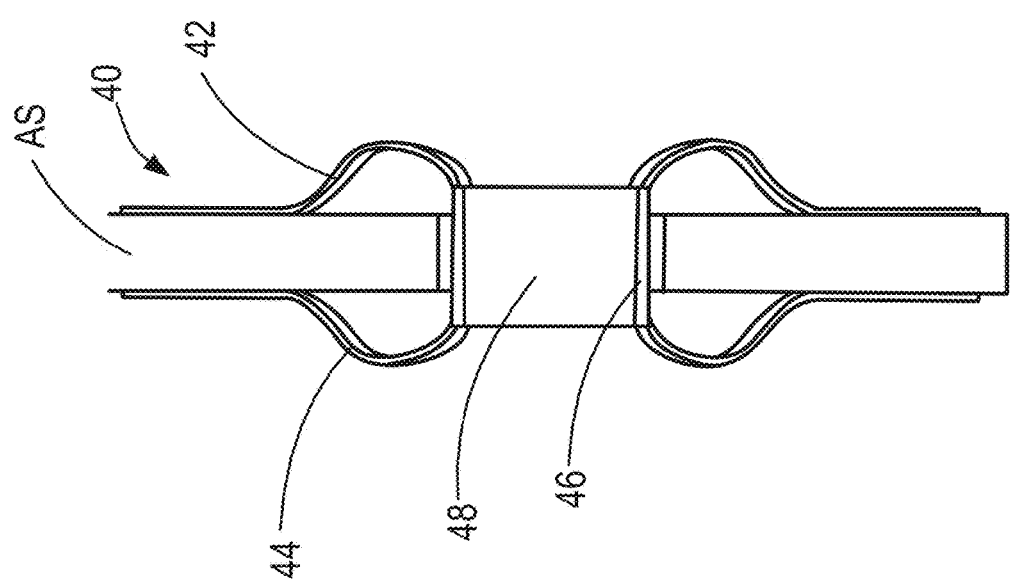
FIG. 4A illustrates an alternative exemplary passage device constructed in accordance with the principles of the present invention.

As illustrated in FIG. 3, which depicts passage device 10 positioned within atrial septum AS from within the left atrium, first end region 12 may include a plurality of support arms coupled circumferentially along outer edges of the middle region of passage device 10. For example, as shown in FIG. 4A, the passage device may be constructed similar to the differential pressure regulating device disclosed in U.S. Pat. No. 8,070,708 to Rottenberg, assigned to the assignee of the instant application, the entire contents of which is incorporated herein by reference. Specifically, passage device 40 of FIG. 4A includes first end portion 42 extending from a proximal edge of middle region 46 into the left atrium, and second end portion 44 extending from a distal edge of middle region 46 into the right atrium. As shown in FIG. 4A, first end region 42 includes a plurality of support arms that extend radially outward from the proximal end of middle region 46, curving away from middle region 46 into the left atrium, then curving back toward atrial septum AS, and further extending parallel to atrial septum AS. Similarly, second end region 44 includes a plurality of support arms that extend radially outward from the distal end of middle region 46, curving away from middle region 46 into the right atrium, then curving back toward atrial septum AS, and further extending parallel to atrial septum AS. In addition, middle portion 46 of passage device 40 may be expanded to a selected shape and size as described above with reference to passage device 10.

As described above, passage device 40 may be designed to anchor an additional medical device within the heart wall. Specifically, as illustrated in FIG. 4B, passage device 40 may be coupled to left atrial blood pressure sensor 49 for measuring blood pressure within the left atrium. Additionally, sensor 49 may effectively plug passage 48 of passage device 40 such that no blood flow is permitted across passage device 40. As will be understood by a person having ordinary skill in the art, various medical devices may be coupled within the lumen of middle region 46 of passage device 40, e.g., a septal occluder, an open atrial septal shunt, a valved atrial septal shunt, or a blood pump.

Figure 5:
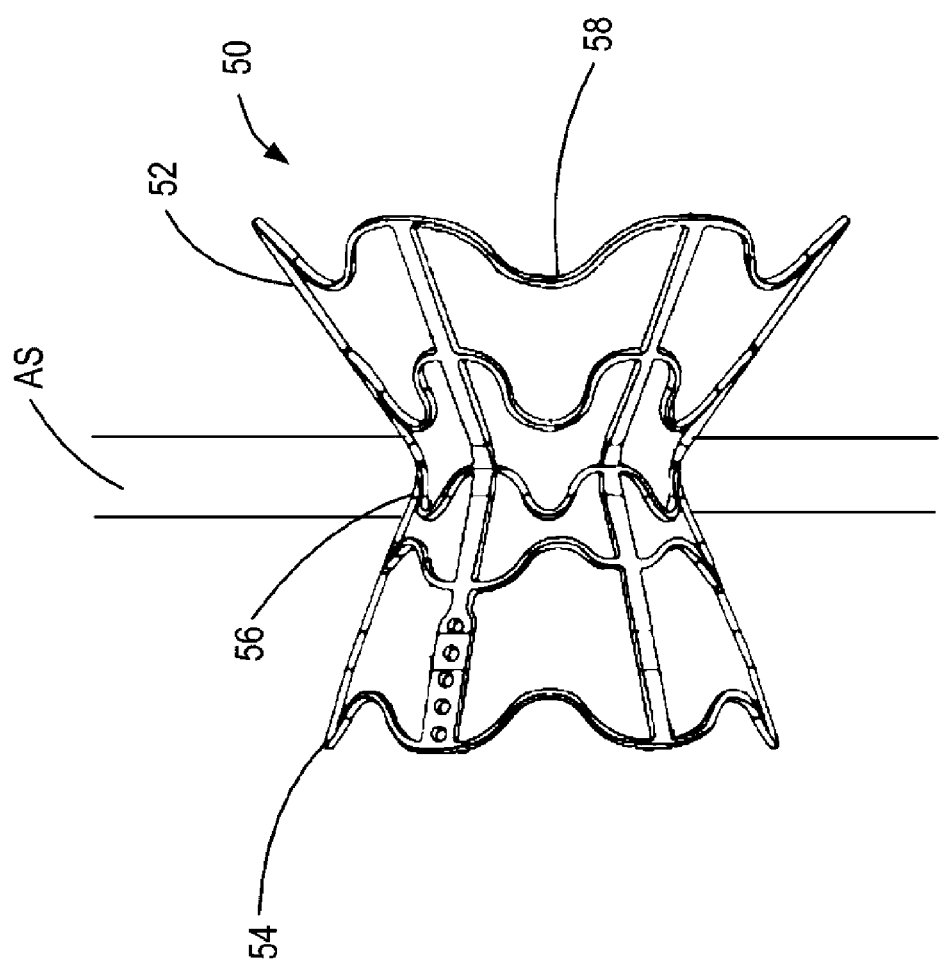
FIG. 5 illustrates another alternative exemplary passage device constructed in accordance with the principles of the present invention.

Referring now to FIG. 5, the passage device may be constructed similar to the differential pressure regulating device disclosed in U.S. Pat. No. 10,076,403 to Eigler, assigned to the assignee of the instant application, the entire contents of which is incorporated herein by reference. Specifically, passage device 50 of FIG. 5 has an hourglass shape, and first end region 52 and second end region 54 are integrally formed with middle region 56. For example, first end region 52, second end region 54, and middle region 56 are formed by a plurality of longitudinal struts interconnected by a plurality of circumferential sinusoidal struts. Further, at least one of first end region 52 or second end region 54 may have at least one of a conical or bell shape. Passage device 50 further may include a layer of biocompatible material disposed on at least middle region 56. In addition, middle portion 56 of passage device 50 may be expanded to a selected shape and size as described above with reference to passage device 10. Moreover, first end portion 52 may be expanded such that it extends into the left atrium at any angle between zero and 90 degrees, and second end portion 54 may be expanded such that it extends into the right atrium at any angle between zero and 90 degrees, as described above with reference to passage device 10.

Figure 6:
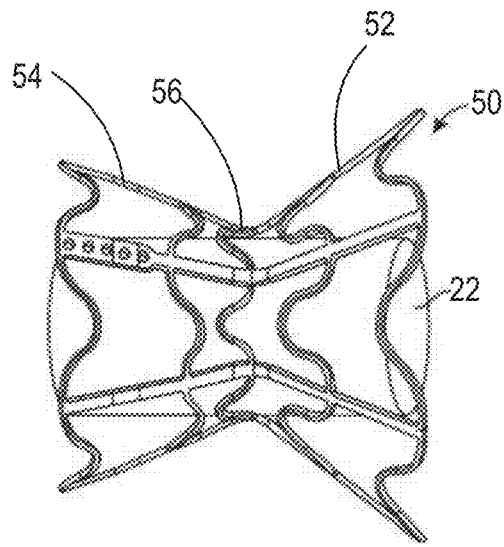
FIGS. 6 and 7 depict the device of FIG. 5 having various alternative embodiments of a shunt disposed therein in accordance with the principles of the present invention.

As described above, passage device 50 may be designed to anchor an additional medical device within the heart wall. Specifically, as illustrated in FIG. 6, conduit 22 is registered with respect to the fossa ovalis of the interatrial septum by passage device 50, thereby providing a shunt across the atrial septum. For example, passage device 50 may be an external, unencapsulated bare metal anchor. Conduit 22 may include a separate encapsulated tubular frame or may comprise a tube of solid material, and may include a variety of geometries to achieve specific characteristics as previously described. Passage device 50 and conduit 22 may be physically affixed to each other prior to insertion in the body by mechanical interference, welding, adhesives, or other well-known means, and preferably includes a skirt that prevents bypass flow between passage device 50 and conduit 22. Alternatively, passage device 50 may be delivered across the septum deployed, and then conduit 22 may be inserted through and deployed within passage device 50 and held in place by mechanical interference or expansion with a balloon, or may be self-expanding. The advantages of such a two-part design are two-fold. First, pannus will grow thick only on the outside surface of passage device 50 because the LA and RA ends of conduit 22 are offset from, and thus do not contact, adjacent cardiac structures. Second, the design creates a longest straight channel for high velocity flow, but limits the ability of paradoxical emboli to transit conduit 22 during a transient pressure gradient reversal.

Figure 7:
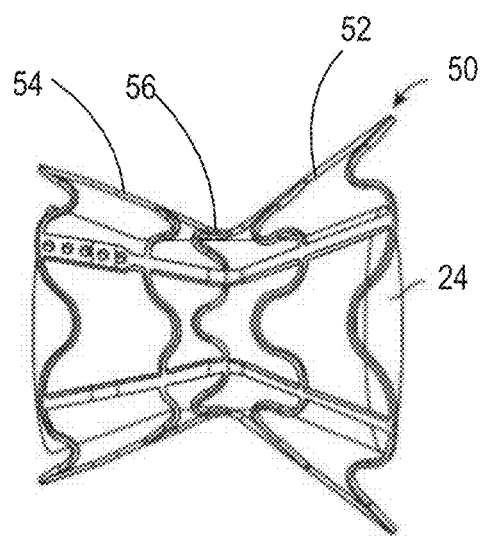

FIG. 7 illustrates another preferred embodiment with benefits similar to that of the shunt of FIG. 6. More specifically, conduit 24 is registered with respect to the fossa ovalis ("FO") of the interatrial septum by passage device 50, thereby providing a shunt across the atrial septum. Conduit 24 may include flared end regions as described above, e.g., to form an hourglass shape in the deployed state. One of ordinary skill in the art will appreciate that the specific shape of the flared end regions may be conical, parabolic, or horned shaped, and may be present at either or both ends of the shunt device depending on the desired hydraulic properties.

The shunt types depicted in FIG. 6 and FIG. 7, or shunts with similar characteristics that would be apparent to one of ordinary skill in the art, may be particularly applicable to the clinical situation where too large an aperture defect has been created in the FO and where interatrial shunting to treat heart failure is required. Consider the case of a patient with severe mitral regurgitation and poor left ventricular function, where it would be clinically desirable to first perform a repair procedure on the mitral valve, e.g. MitraClip® of mitral annuloplasty by the percutaneous transseptal approach, followed by interatrial shunt placement. These mitral valve procedures currently use a 23Fr I.D. (~8 mm O.D) guiding catheter to cross the FO. After mitral repair, an anchor with an outer minimal diameter matching the larger aperture defect caused by the prior procedure may be implanted, wherein the conduit as a smaller diameter desirable for shunting (e.g. 5.0 to 6.5 mm). Likewise, such shunts advantageously may be used where, during the transseptal procedure, the FO has been torn, thus creating a larger aperture defect than required for various shunt embodiments. Again, a shunt of the kind described with respect to FIG. 6 or 7 could be used to address such a situation.

Figure 8A:
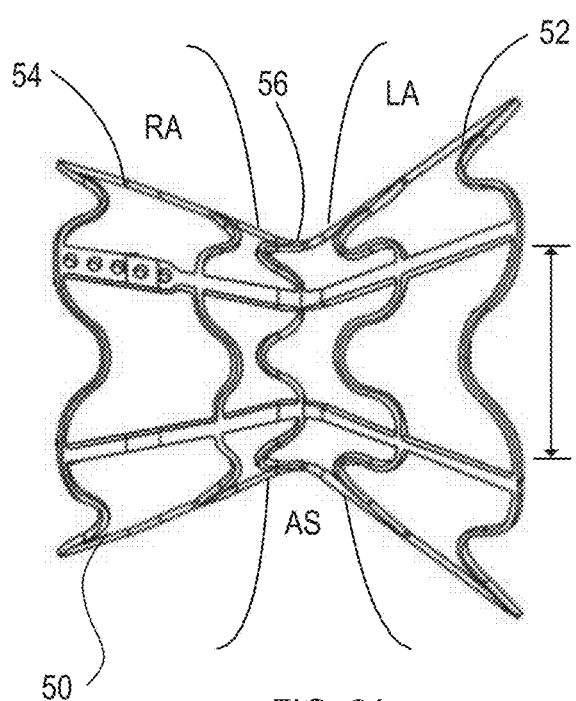
FIGS. 8A and 8B depict the device of FIG. 5 having a stent subsequently disposed therein in accordance with the principles of the present invention.
Figure 8B:
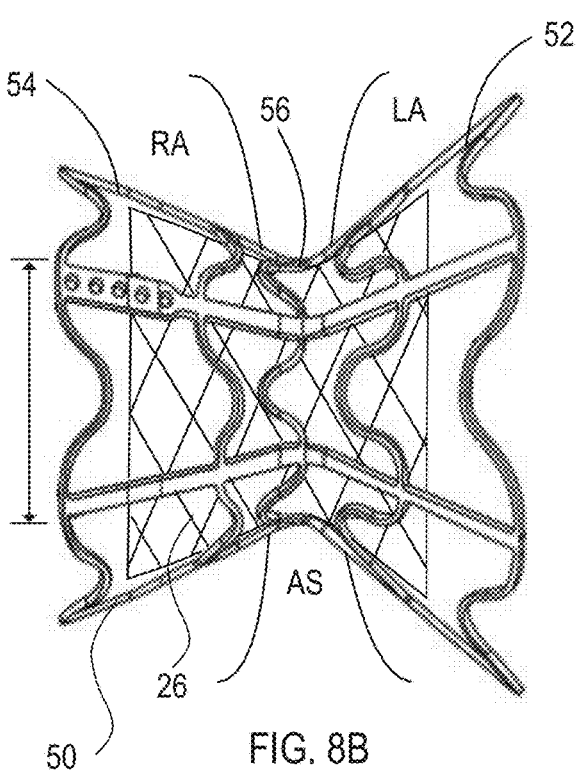

Referring now to FIGS. 8A and 8B, additional alternative embodiments are described, where passage device 50 is positioned within the fossa ovalis of the atrial septum as described above, and an expandable metal stent is subsequently placed within the lumen of passage device 50 and expanded to enlarge the cross-sectional area at middle region 56 of passage device 50, for example, after passage device 50 has been chronically deployed. As illustrated in FIG. 8A, passage device 50 is first positioned within a puncture of the atrial septum AS such that first end region 52 extends within left atrium LA, and second end region 54 extends within right atrium RA. Subsequently, as illustrated in FIG. 8B, expandable stent 26 may be deployed within the lumen of passage device 50. Stent 26 may be balloon-expandable or self-expanding. Stent 26 may be an unencapsulated bare metal mesh stent. In accordance other aspects of the present invention, stent 26 may be a drug-eluting mesh stent or an encapsulated mesh stent. In addition, stent 26 may include flared end regions to form an hourglass shape in the deployed state and conform to the shape of passage device 50.

By comparing FIGS. 8A and 8B, introduction of expandable stent 26 within the lumen of passage device 50 causes the diameter at middle region 56 of passage device 50 to increase over time. For example, stent 26 may be self-expanding upon deployment, or an inflatable balloon may be positioned within the lumen of stent 26 and inflated to expand stent 26, and consequently, passage device 50. The balloon is then removed and mechanical interference may physically affix stent 26 to passage device 50 within the atrial septum AS. In addition, stent 26 stent may be coupled to passage device 50 such that it may be periodically removed from passage device 50 while passage device 50 remains anchored within atrial septum AS, if necessary, and replaced with another stent, such as when tissue ingrowth interferes with performance of the stent. Further, stent 26 may be removed any time there is a need to pass a catheter or other medical device between the heart chambers. As will be understood by a person having ordinary skill in the art, various medical devices may be coupled within the lumen of middle region 56 of passage device 50, e.g., a septal occluder, a valved atrial septal shunt, a left atrial blood pressure sensor, or a blood pump.

Referring now to FIGS. 9A to 9C, adjustment of the diameter of the passage of a middle region of an exemplary passage device in situ is described. As shown in FIG. 9A, middle region 16 of passage device 10 initially may be concaved inward toward the longitudinal axis of passage device 10, thereby reducing the cross-sectional area of passage 20 of middle region 16. Accordingly, a balloon catheter may be delivered within passage 20 of passage device 10, and inflated to adjust the cross-sectional area across passage 20. For example, as shown in FIG. 9B, the balloon catheter may be inflated until middle region 16 of passage device 10 is linear, parallel to the longitudinal axis of passage device 10. Further, as shown in FIG. 9C, the balloon catheter may be inflated until middle region 16 of passage device 10 is concaved outward away from the longitudinal axis of passage device 10. The size of passage 20 may be selected dependent of the clinical procedure being performed by the surgeon. As will be understood by a person having ordinary skill in the art, other expanding devices may be used to apply force against middle region 16 to thereby adjust the size of passage 20 of passage device 10.

Figure 10C:
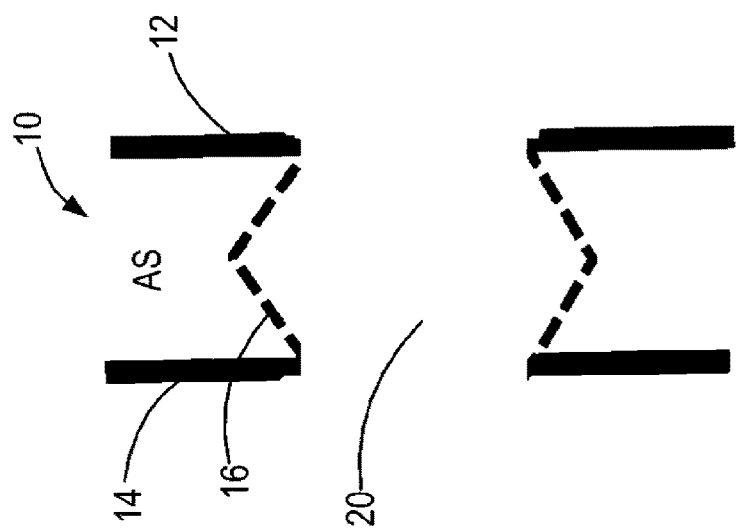
FIGS. 10A to 10C are cross-sectional views of an alternative embodiment of a passage device wherein the passage through the device is adjusted in situ in accordance with the principles of the present invention.
Figure 10B:
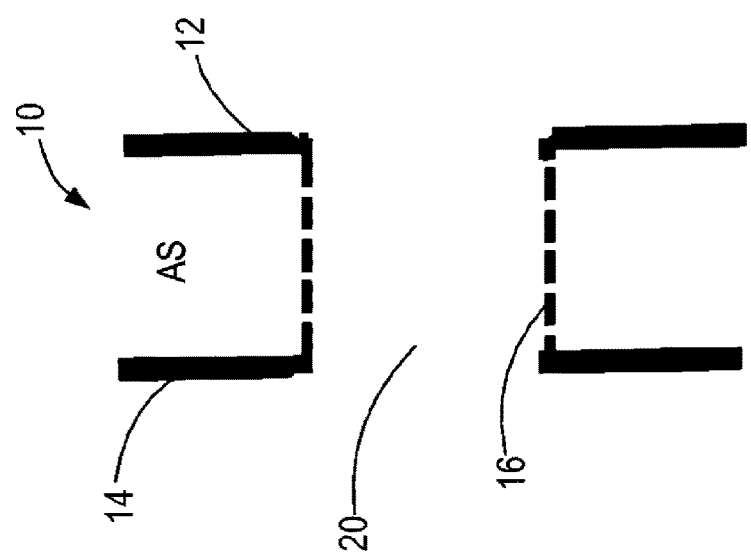
Figure 10A:
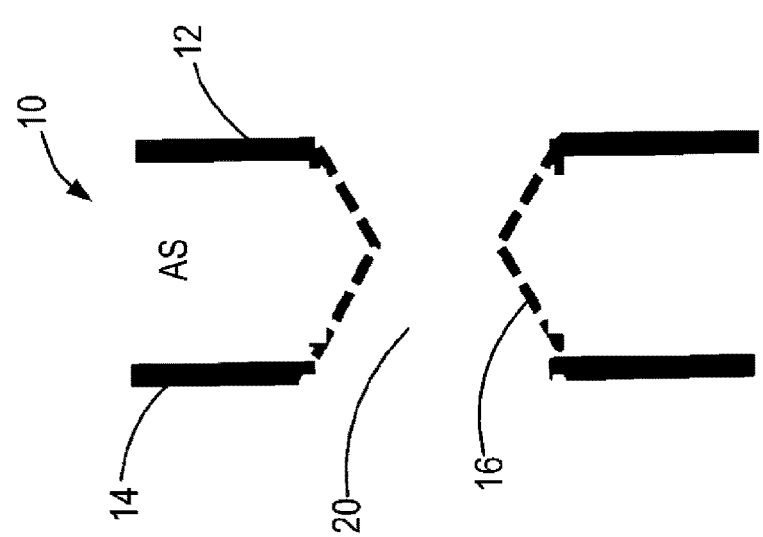

Referring now to FIGS. 10A to 10C, adjustment of the diameter of the passage of a middle region of an alternative exemplary passage device in situ is described. As shown in FIG. 10A, middle region 16 of passage device 10 initially may be pointed inward toward the longitudinal axis of passage device 10, e.g., in a triangular manner, thereby reducing the cross-sectional area of passage 20 of middle region 16. Accordingly, a balloon catheter may be delivered within passage 20 of passage device 10, and inflated to adjust the cross-sectional area across passage 20. For example, as shown in FIG. 10B, the balloon catheter may be inflated until middle region 16 of passage device 10 is linear, parallel to the longitudinal axis of passage device 10. Further, as shown in FIG. 10C, the balloon catheter may be inflated until middle region 16 of passage device 10 is pointed outward away from the longitudinal axis of passage device 10, e.g., in a triangular manner. The size of passage 20 may be selected dependent of the clinical procedure being performed by the surgeon. As will be understood by a person having ordinary skill in the art, other expanding devices may be used to apply force against middle region 16 to thereby adjust the size of passage 20 of passage device 10.

Figure 11C:
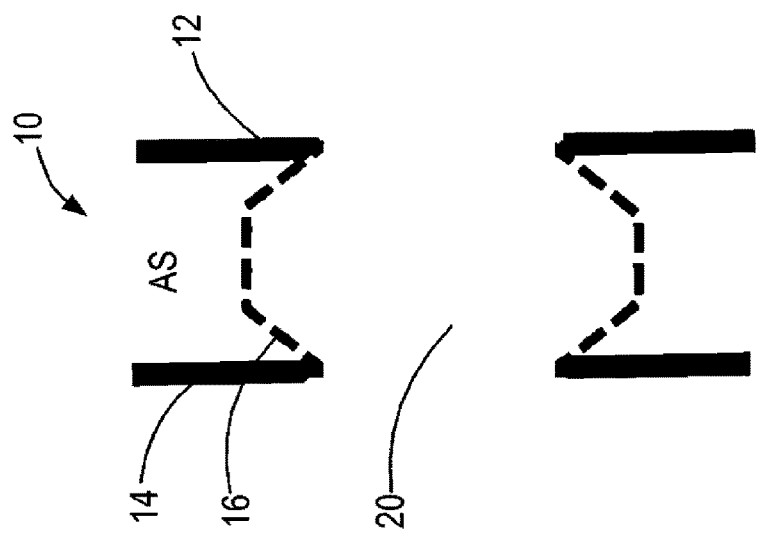
FIGS. 11A to 11C are cross-sectional views of another alternative embodiment of a passage device wherein the passage through the device is adjusted in situ in accordance with the principles of the present invention.
Figure 11B:
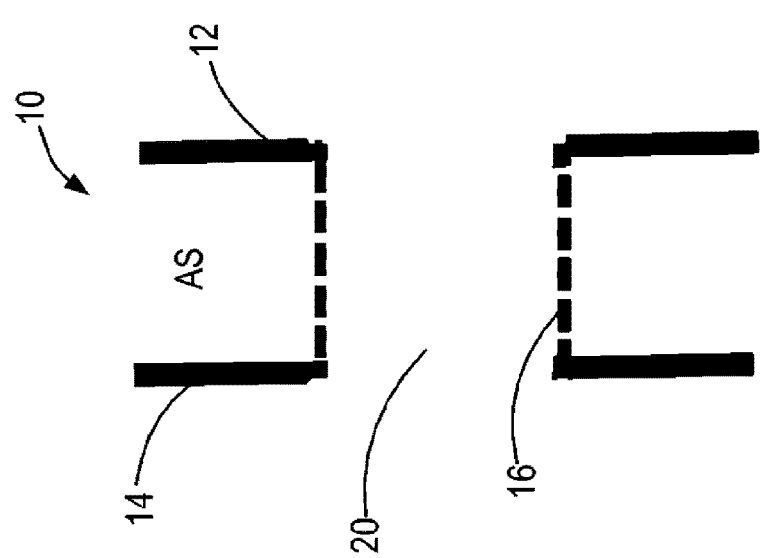
Figure 11A:
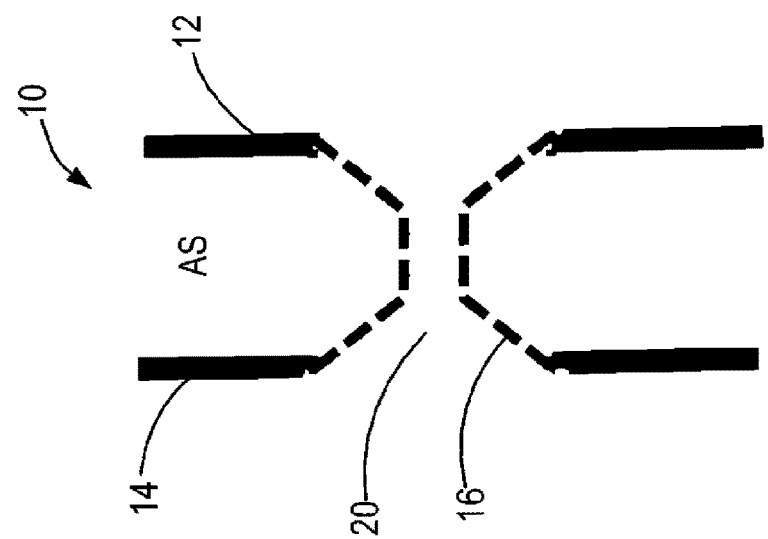

Referring now to FIGS. 11A to 11C, adjustment of the diameter of the passage of a middle region of another alternative exemplary passage device in situ is described. As shown in FIG. 11A, middle region 16 of passage device 10 initially may be trapezoidally pointed inward toward the longitudinal axis of passage device 10, thereby reducing the cross-sectional area of passage 20 of middle region 16. Accordingly, a balloon catheter may be delivered within passage 20 of passage device 10, and inflated to adjust the cross-sectional area across passage 20. For example, as shown in FIG. 11B, the balloon catheter may be inflated until middle region 16 of passage device 10 is linear, parallel to the longitudinal axis of passage device 10. Further, as shown in FIG. 11C, the balloon catheter may be inflated until middle region 16 of passage device 10 is trapezoidally pointed outward away from the longitudinal axis of passage device 10. The size of passage 20 may be selected dependent of the clinical procedure being performed by the surgeon. As will be understood by a person having ordinary skill in the art, other expanding devices may be used to apply force against middle region 16 to thereby adjust the size of passage 20 of passage device 10. In addition, passage device 10 may include one or more sensors for measuring blood flow through passage 20 between the left atrium and the right atrium, such that middle region 16 may be adjusted from responsive to the measured blood flow. For example, the one or more sensors may be at least one of a pressure sensor, ultrasound probe, blood flow sensor, temperature sensor or oxygen saturation sensor.

Figure 12A:
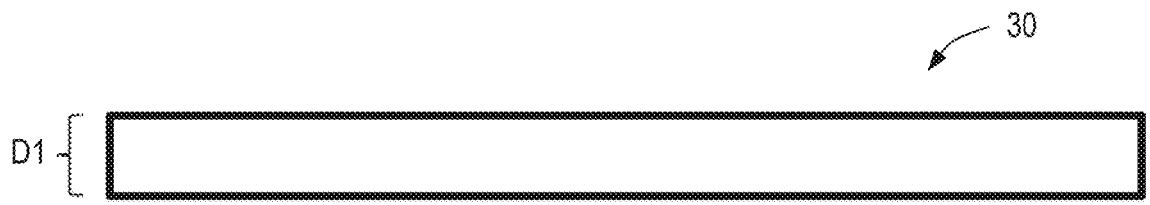
FIG. 12A illustrates an exemplary dog bone shaped balloon catheter, in a deflated state, for transitioning the end regions of a passage device from a compressed delivery state to an expanded deployed state, constructed in accordance with the principles of the present invention.
Figure 12B:
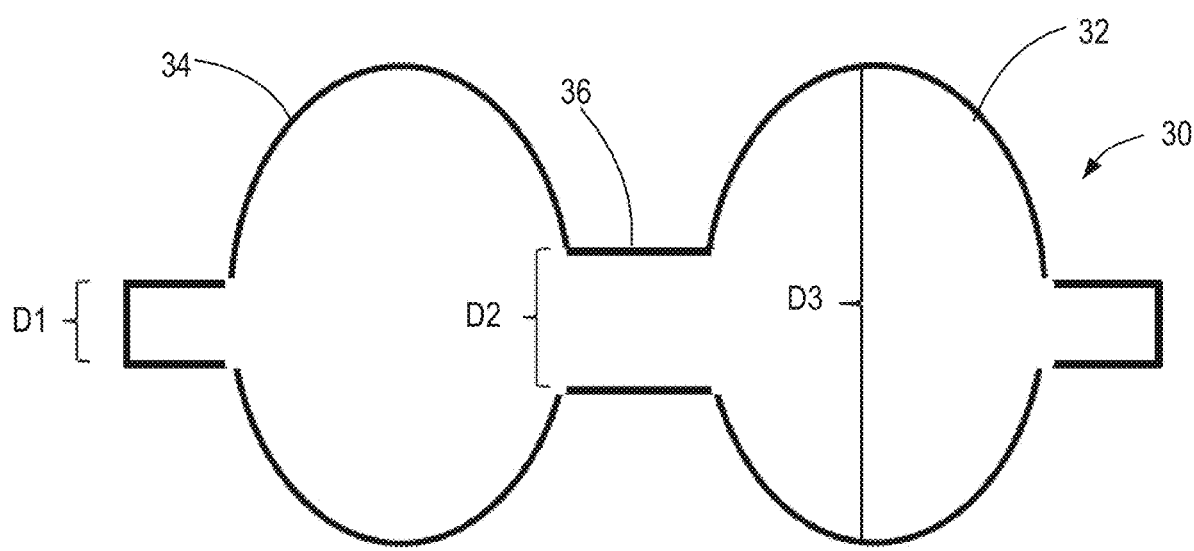
FIG. 12B illustrates the exemplary dog bone shaped balloon catheter of FIG. 12A in an inflated state.
Figure 12C:
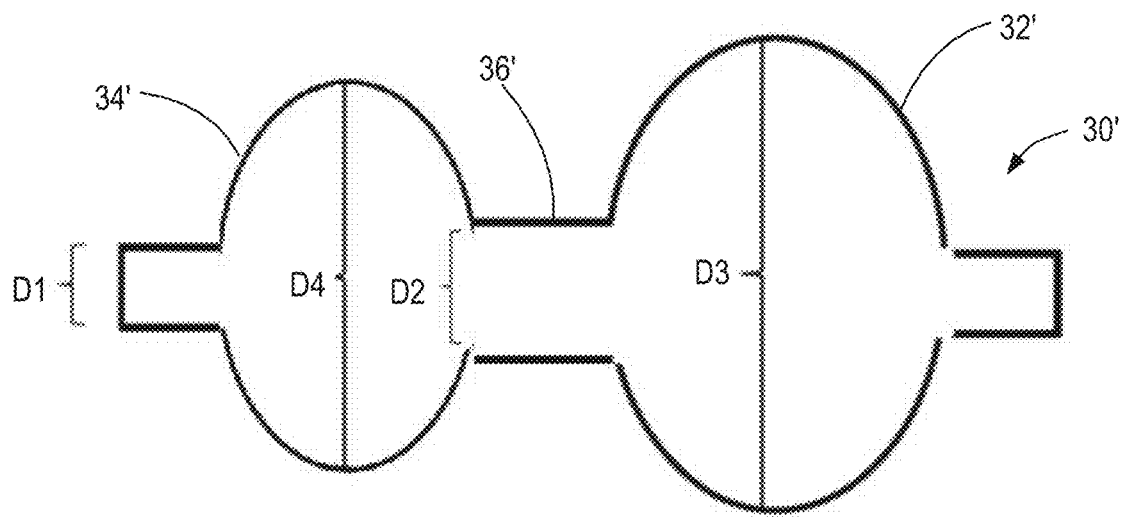
FIG. 12C illustrates another exemplary dog-bone shaped catheter constructed in accordance with the principles of the present invention.

Referring now to FIGS. 12A and 12B, an exemplary dog bone shaped balloon catheter is described. As shown in FIG. 12A, balloon catheter 30 may have an initial diameter D1. For example, D1 may be any size between, e.g., 0.5 mm to 0.5 cm, 0.5 mm to 1 cm, or 0.1 mm to 2 cm. As shown in FIG. 12B, balloon catheter 30 may be inflated such that proximal portion 32 and distal portion 34 expand to have diameter D3, to thereby adjust the angle and cross-sectional area of the first and second end regions of the passage device as described in further detail below with reference to FIGS. 13A to 13C. For example, D3 may be any size between, e.g., 1 mm to 2 cm, 1 mm to 5 cm, or 0.5 mm to 10 cm. In addition, middle portion 36 may be expanded to have diameter D2. For example, D2 may be any size between, e.g., 1 mm to 1 cm, 1 mm to 2 cm, or 0.5 mm to 5 cm. In accordance with another aspect of the present invention, balloon catheter 30 may be formed such that upon inflation, the proximal portion and the distal portion expand to have different diameters from each other. For example, as shown in FIG. 12C, balloon catheter 30' may be inflated such that proximal portion 32' expands to have diameter D3, whereas distal portion 34' expands to have diameter D4. For example, D4 may be any size between, e.g., 1 mm to 2 cm, 1 mm to 5 cm, or 0.5 mm to 10 cm.

Figure 13A:
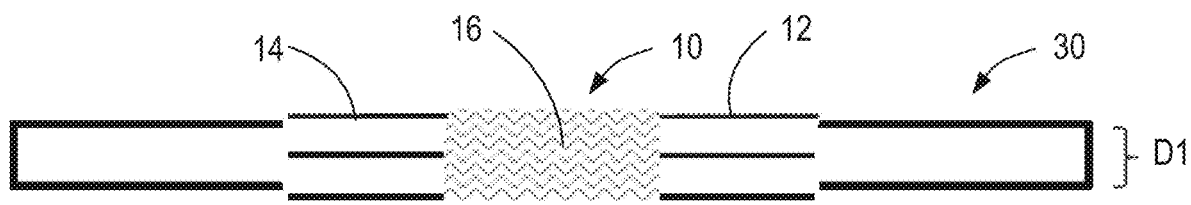
FIGS. 13A to 13C illustrate the steps of using the exemplary dog bone shaped balloon catheter of FIG. 12A to transition the end regions of a passage device from a compressed delivery state to an expanded deployed state.
Figure 13B:
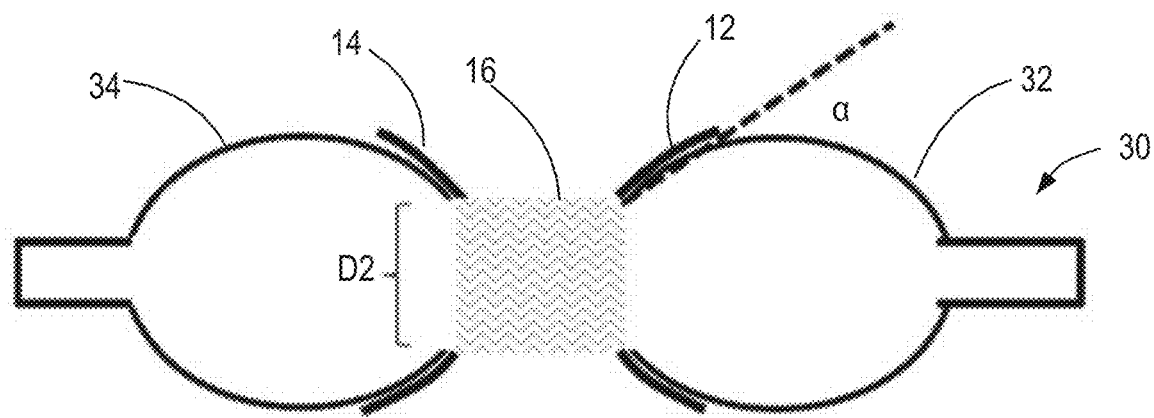
Figure 13C:
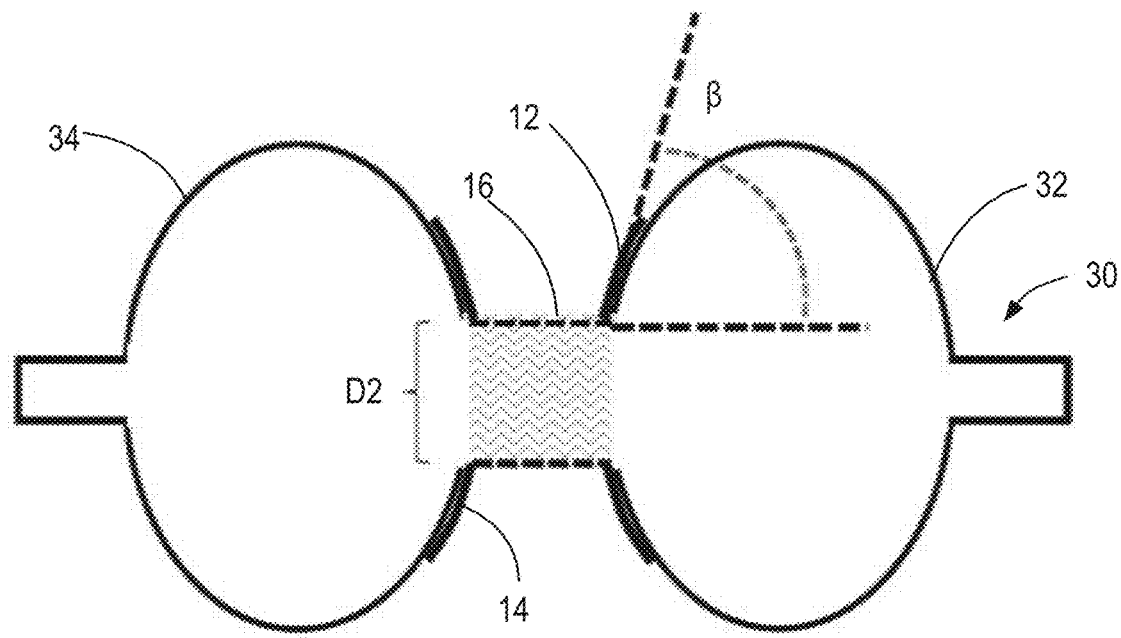

Referring now to FIGS. 13A to 13C, balloon catheter 30 may be used to adjust the angle and cross-sectional area of first end region 12, second end region 14, and middle region 16 of passage device 10. As shown in FIG. 13A, balloon catheter 30 is first introduced within passage 20 of passage device 10 in a deflated state after passage device 10 is positioned within the heart wall. As shown in FIG. 13B, balloon catheter may be inflated such that middle region 16 expands to have diameter D2. Accordingly, as first portion 32 and second portion 34 expand upon inflation of balloon catheter 30, first portion 32 and second portion 34 will apply a force against first end region 12 and second end region 14, respectively, thereby causing first end region 12 and second end region 14 to expand and extend into their respective atria at angle α relative to the longitudinal axis of passage device 10. For example, α may be between zero and 45 degrees, preferably 30 to 45 degrees. In addition, as shown in FIG. 13C, balloon catheter 30 may be further inflated such that first portion 32 and second portion 34 expand and apply an additional force against first end region 12 and second end region 14, respectively, thereby causing first end region 12 and second end region 14 to expand and extend into their respective atria at angle β relative to the longitudinal axis of passage device 10. For example, β may be between 45 and 90 degrees.

Figure 14A:
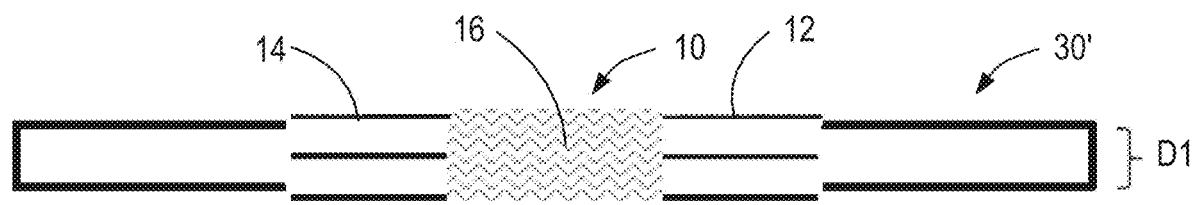
FIGS. 14A and 14B illustrate the steps of using the exemplary dog bone shaped balloon catheter of FIG. 12C to transition the end regions of a passage device from a compressed delivery state to an expanded deployed state.
Figure 14B:
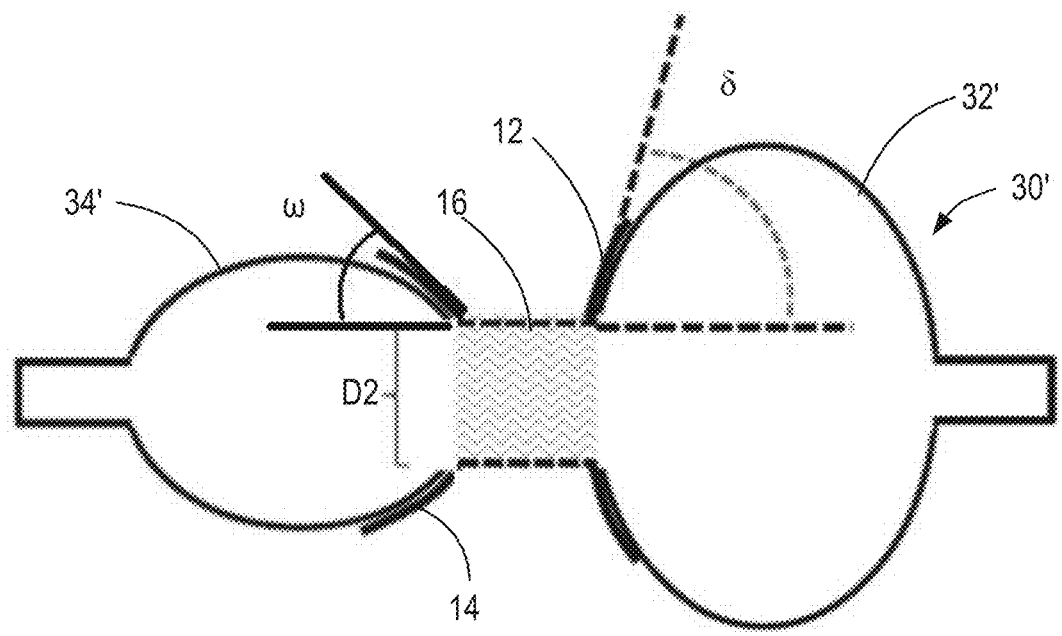

Referring now to FIGS. 14A and 14B, balloon catheter 30' may be used to asymmetrically adjust the angle and cross-sectional area of first end region 12, second end region 14, and middle region 16 of passage device 10. As shown in FIG. 14A, balloon catheter 30' is first introduced within passage 20 of passage device 10 in a deflated state after passage device 10 is positioned within the heart wall. As shown in FIG. 14B, balloon catheter may be inflated such that middle region 16 expands to have diameter D2. Accordingly, as first portion 32' expands upon inflation of balloon catheter 30', first portion 32' will apply a force against first end region 12, thereby causing first end region 12 to expand and extend into the left atrium at angle δ relative to the longitudinal axis of passage device 10. For example, δ may be between 45 and 90 degrees. In addition, as second portion 34' expands upon inflation of balloon catheter 30', second portion 34' will apply a force against second end region 14, thereby causing second end region 14 to expand and extend into the right atrium at angle ω relative to the longitudinal axis of passage device 10. For example, ω may be between zero and 45 degrees, preferably 30 to 45 degrees.

Figure 15A:
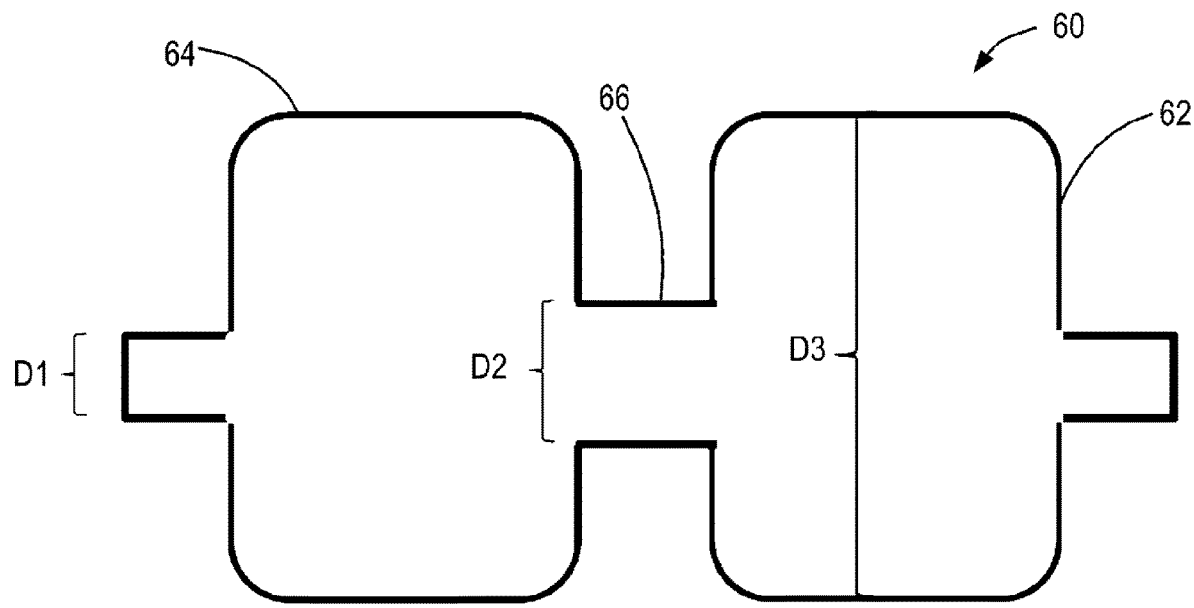
FIG. 15A illustrates an exemplary quadrilateral dog bone shaped balloon catheter for transitioning the end regions of a passage device from a compressed delivery state to an expanded deployed state, constructed in accordance with the principles of the present invention.
Figure 15B:
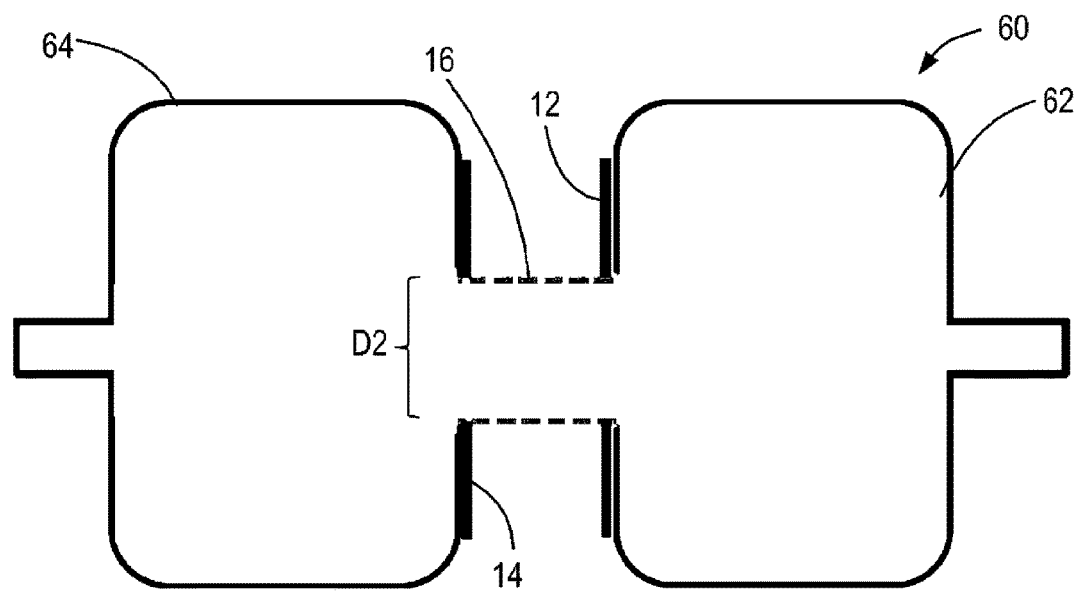
FIG. 15B illustrates the exemplary quadrilateral dog bone shaped balloon catheter of FIG. 15A being used to transition the end regions of a passage device from a compressed delivery state to an expanded deployed state.

Referring now to FIGS. 15A and 15B, an exemplary quadrilateral dog bone shaped balloon catheter is described. Balloon catheter 60 may be constructed similar to balloon catheter 30, except that first portion 62 and second portion 64 have a quadrilateral shape upon inflation of balloon catheter 60. Accordingly, as shown in FIG. 15A, balloon catheter 60 may be inflated such that proximal portion 62 and distal portion 64 expand to have diameter D3, and middle portion 66 expands to have diameter D2. As shown in FIG. 15B, upon inflation of balloon catheter 60 within passage 20 of passage device 10, first portion 62 and second portion 64 apply a force against first end region 12 and second end region 14, respectively, thereby causing first end region 12 and second end region 14 to expand and extend into their respective atria at an angle of 90 degrees relative to the longitudinal axis of passage device 10. As will be understood by a person having ordinary skill in the art, first and second portions of the balloon catheter may be preformed to have various shapes and sizes upon inflation of the balloon catheter to achieve the desired adjustment of the first end region, second end region, and middle region of the passage device.

Figure 16A:
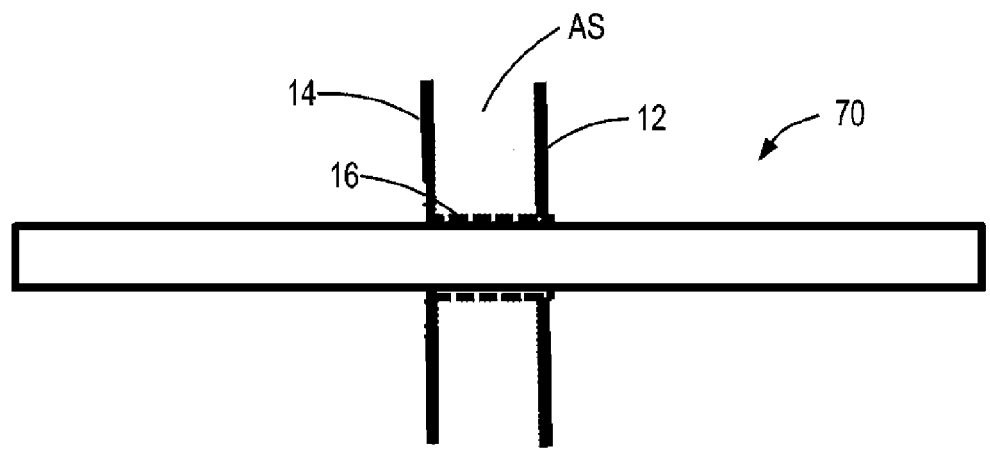
FIGS. 16A to 16C illustrate the steps of using an exemplary balloon catheter to adjust the size of the passage of a passage device in accordance with the principles of the present invention.
Figure 16B:
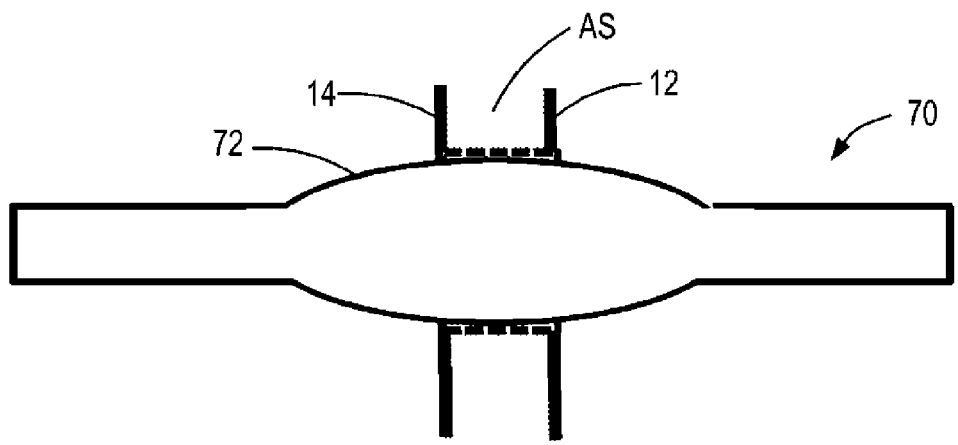
Figure 16C:
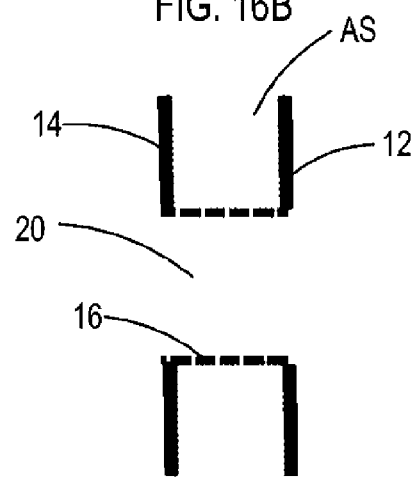

Referring now to FIGS. 16A to 16C, an exemplary balloon catheter for adjusting the size of the passage of the middle region of the passage device in situ is provided. As shown in FIG. 16A, balloon catheter 70 is first introduced through passage 20 of passage device 10 in a deflated state after passage device 10 is deployed within atrial septum AS. Then, as shown in FIG. 16B, balloon catheter 70 is inflated such that expandable portion 72 of balloon catheter 70 expands to a desired size. As expandable portion 72 expands, expandable portion 72 applies a force against middle region 16, thereby causing the diameter of passage 20 of passage device 10 to increase. Balloon catheter 70 may be inflated until passage 20 reaches a desired size dependent on the clinical procedure being performed by the surgeon. Balloon catheter 70 is then removed from within passage 20 of passage device 10, leaving passage 20 at the desired size due to the deformable plastic properties of middle region 16 as shown in FIG. 16C.

Figure 17B:
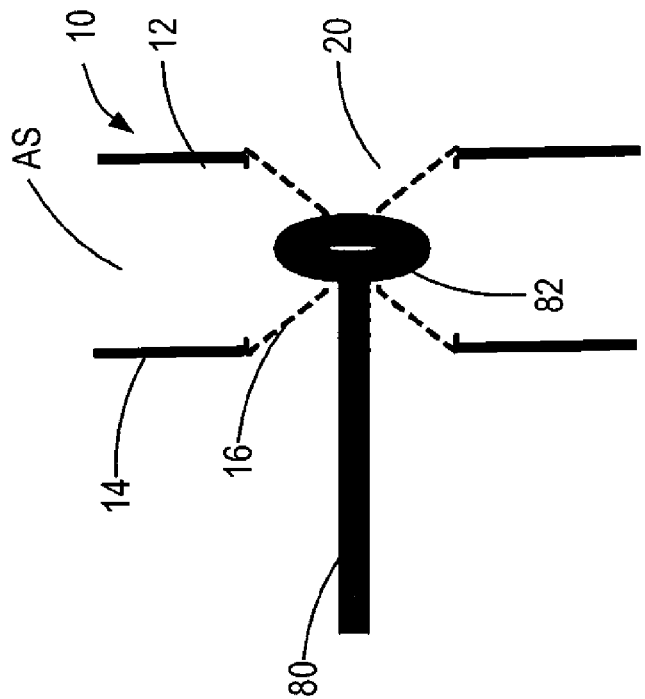
FIGS. 17A and 17B illustrate the steps of using a snare to adjust the size of the passage of a passage device in accordance with the principles of the present invention.
Figure 17A:
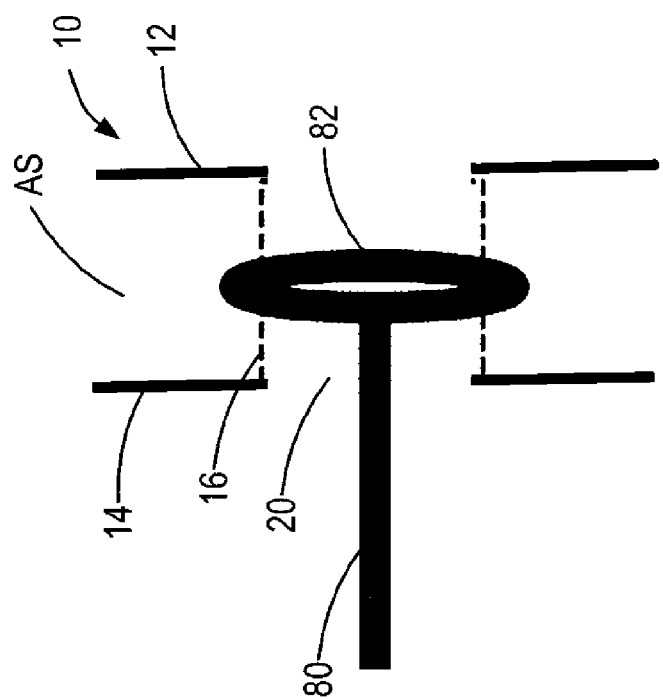

Referring now to FIGS. 17A and 17B, the steps of using a snare to adjust the size of the passage of a passage device in accordance with the principles of the present invention is provided. Snare 80 may be advanced over passage device 10 when passage device 10 is deployed within atrial septum AS such that middle region 16 is positioned within snare hoop 82 of snare 80. As shown in FIG. 17A, snare hoop 82 has an initial diameter such that middle region 16 fits within snare hoop 82 in an uncompressed state. As shown in FIG. 17B, snare 80 may be actuated such that the diameter of snare hoop 82 decreased from the initial diameter to a smaller diameter, thereby causing middle region 16 to compress, and accordingly, passage 20 to decrease in size. For example, snare hoop 82 may be formed of a wire that is exposed through a lumen of a tubular catheter of snare 80, wherein the size of snare hoop 82 may be adjusted by retracting the wire through the lumen of the tubular catheter. As will be understood by a person having ordinary skill in the art, snare 80 may be actuated to selectively adjust the size of snare hoop 82, to thereby control the size of passage 20 of passage device 10, and accordingly, the flowrate across passage device 10. The size of passage 20 also may be adjusted to accommodate clinical procedure tools required by the surgeon. In addition, a balloon catheter may be used in conjunction with snare 80 to ensure that middle region 16 is compressed to the desired passage size. For example, the balloon catheter may be delivered within passage 20 of passage device 10 when middle region 16 is within snare hoop 82, and inflated to the desired passage size. Accordingly, snare 80 may be actuated such that the opening of snare hoop 82 is reduced to conform with the inflated balloon catheter, thereby achieving the desired passage size of middle region 16.

Figure 18A:
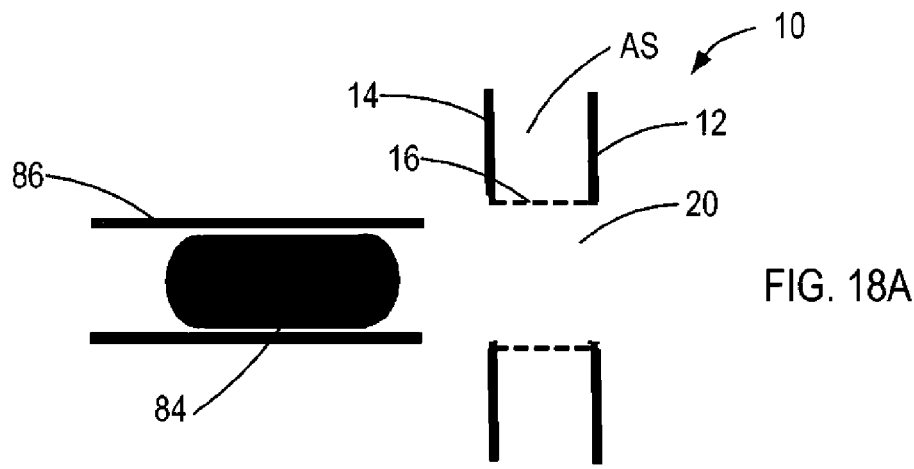
FIGS. 18A to 18C illustrate the steps of subsequently placing a medical device within the device of FIG. 1A in accordance with the principles of the present invention.
Figure 18B:
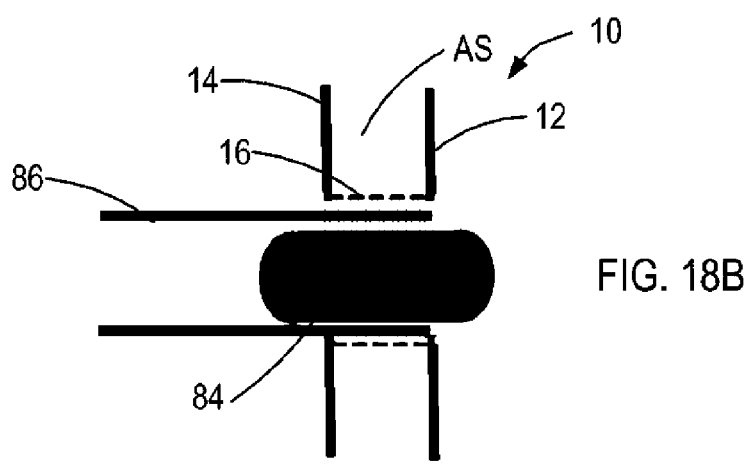
Figure 18C:
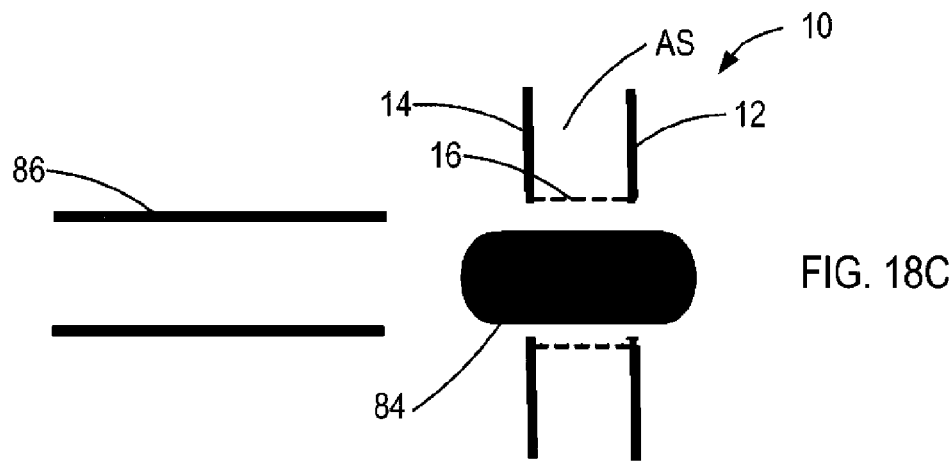

Referring now to FIGS. 18A to 18C, the steps of subsequently placing a medical device within the device of FIG. 1A in accordance with the principles of the present invention is provided. As described above, passage device 10 may be designed to anchor an additional medical device within the heart wall. As shown in FIG. 18A, medical device 84 may be disposed within sheath 86 for delivery to passage device 10. As illustrated in FIG. 18B, sheath 86 is delivered through passage 20 of passage device 10 such that medical device 84 is aligned with middle region 16 of passage device 10. Sheath 86 may then be retracted, leaving medical device 84 positioned within passage 20, as shown in FIG. 18C. Medical device 84 may be coupled to passage device 10 via techniques readily known in the art. Medical device 84 may be, e.g., a septal occluder, an open atrial septal shunt, a valved atrial septal shunt, a left atrial blood pressure sensor, or a blood pump. In addition, medical device 84 may be removed and replaced according to the needs of the patient and the clinical procedure.

Figure 19A:
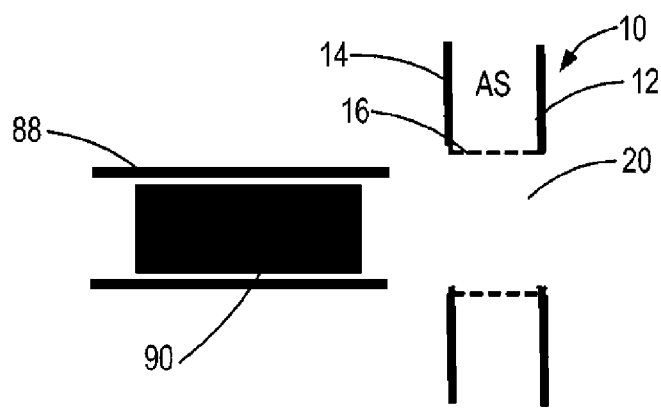
FIGS. 19A to 19D illustrate the steps of subsequently placing a medical device having expandable ends within the device of FIG. 1A in accordance with the principles of the present invention.
Figure 19B:
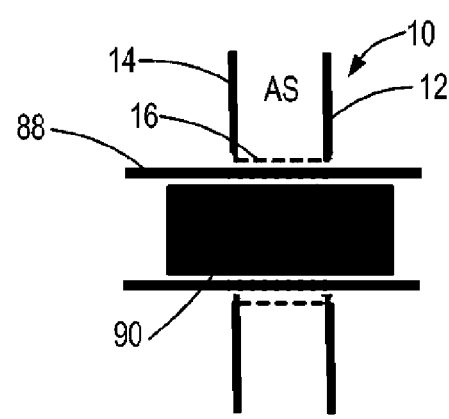

Referring now to FIGS. 19A to 19D, the steps of subsequently placing a medical device having expandable ends within the device of FIG. 1A in accordance with the principles of the present invention is provided. As shown in FIG. 19A, medical device 90 may be disposed within sheath 88 for delivery to passage device 10. Medical device 90 includes first expandable portion 92 sized and shaped to be disposed within the left atrium, and second expandable portion 94 sized and shaped to be disposed within the right atrium upon deployment of medical device 90. As shown in FIG. 19A, first and second expandable portions 92, 94 may be disposed within sheath 88 in a compressed delivery state. As illustrated in FIG. 19B, sheath 88 is delivered through passage 20 of passage device 10 such that medical device 90 is aligned with middle region 16 of passage device 10.

Figure 19C:
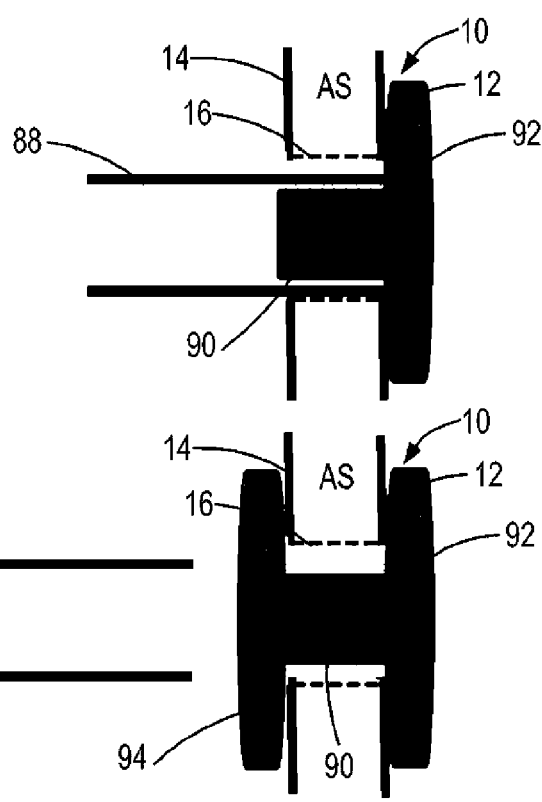

Sheath 88 may then be partially retracted, exposing first expandable portion 92 beyond the opening of sheath 88 such that first expandable portion 92 transitions from the compressed delivery stated to an expanded deployed state within the left atrium, as shown in FIG. 19C. For example, first expandable portion 92 may be self-expanding. Sheath 88 and medical device 90 are positioned within passage 20 of passage device 10 such that first expandable portion 92 of medical device 90 is positioned adjacent first end region 12 of passage device 10 within the left atrium.

Figure 19D:
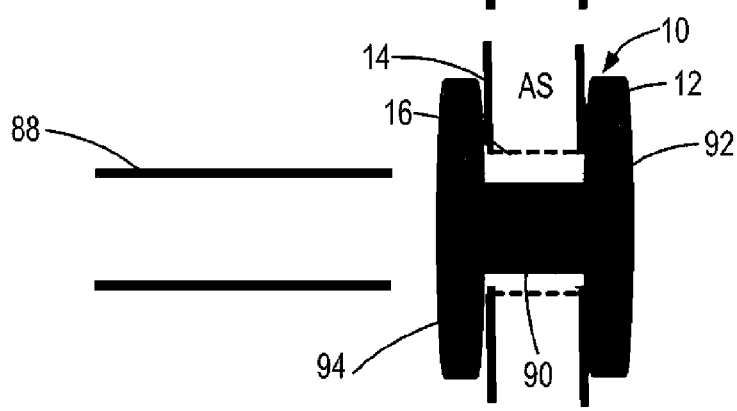

As shown in FIG. 19D, sheath 88 may be further retracted, exposing second expandable portion 94 beyond the opening of sheath 88 such that second expandable portion 94 transitions from the compressed delivery stated to an expanded deployed state within the right atrium. For example, second expandable portion 94 may be self-expanding. In the expanded state, first and second expandable portions 92, 94 of medical device 90 sandwich passage device 10 within atrial septum AS, thereby assisting anchoring of medical device 90 within passage device 10 at atrial septum AS.

Figure 20:
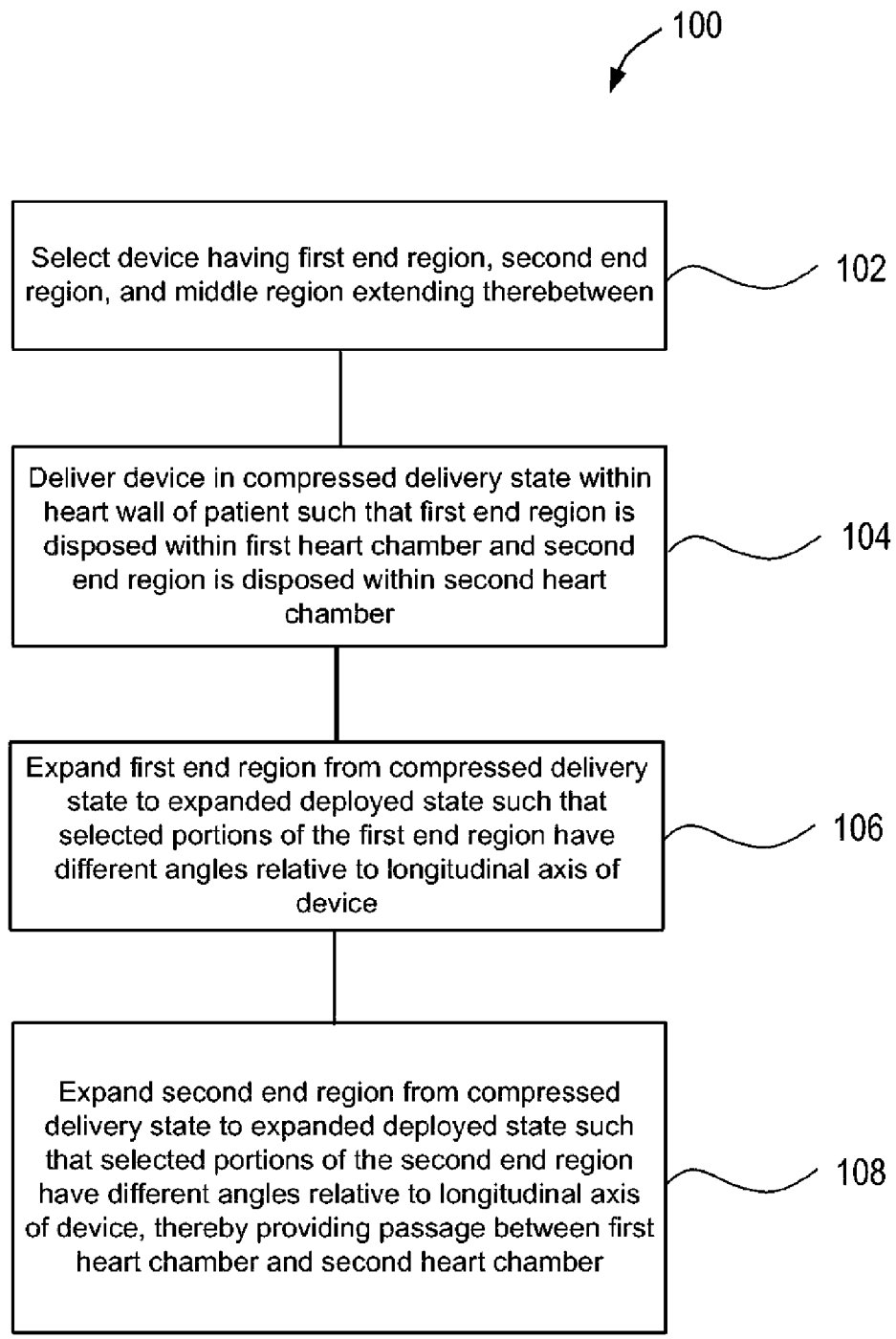
FIG. 20 is a flow chart of an exemplary method for transitioning the end regions of a passage device from a compressed delivery state to an expanded deployed state in accordance with the principles of the present invention.

In accordance with another aspect of the present invention, exemplary method 100 for transitioning the end regions of a passage device from a compressed delivery state to an expanded deployed state in accordance with the principles of the present invention is provided. As shown in FIG. 20, at step 102, a passage device is selected, e.g., any of the passage devices described above. The passage device includes a first end region, a second end region, and a middle region extending between the first and second end regions. The passage device may be transitioned to a compressed delivery state and disposed within a delivery sheath for percutaneous delivery. At step 104, the passage device is delivered to the target site, e.g., an atrial septum between left and right atria, in the compressed delivery state. The sheath may be retracted to deploy the passage device at the atrial septum such that the first end region is disposed within the left atrium, the second end region is disposed within the right atrium, and the middle region of the passage device is disposed within an opening in the atrial septum.

At step 106, a balloon catheter, e.g., any of the balloon catheters described above, or any other suitable expanding tool, is introduced through the lumen of the passage device. The balloon catheter is then inflated to expand the first end region from the compressed delivery state to an expanded deployed state in the left atrium such that selected portions of the first end region have different angles relative to the longitudinal axis of the passage device. For example, the balloon catheter may have multiple inflatable portions, each in fluid communication with its own fluid lumen of the balloon catheter, so that the selected portions of the first and second end regions may be expanded to the desired angle for that selected portion.

At step 108, inflation of the balloon catheter causes the second end region to expand from the compressed delivery state to an expanded deployed state in the right atrium such that selected portions of the second end region have different angles relative to the longitudinal axis of the passage device. As will be understood by a person having ordinary skill in the art, step 106 and step 108 may occur simultaneously upon inflation of the balloon catheter. In addition, the first and second end regions may be expanded to extend within their respective atria at the same angle relative to the longitudinal axis of the passage device. The balloon catheter may then be removed such that the middle region of the passage device maintains its adjusted size.

While various illustrative embodiments of the invention are described above, it will be apparent to one skilled in the art that various changes and modifications may be made herein without departing from the invention. For example, the inventive devices and methods may be used following, e.g., a mitral valve ("MV") repair procedure, where the passage device is placed within the mitral valve having a desired passage size. MV repair may result in a larger than optimal orifice, and thus the adjustable passage device may be used to optimize flow across the MV, which may be readjusted later as described above in accordance with the principles of the present invention.

What is claimed:

1. A device for providing a passage between a first heart chamber and a second heart chamber, the device comprising:
a middle region having first and second ends, a lumen extending therethrough, and a longitudinal axis aligned with the lumen;
a first end region coupled to the first end, the first end region configured to be delivered in the first heart chamber in a compressed delivery state and to transition to a deployed state therein, first selected portions of the first end region are configured to be independently, selectively deformable by a first force such that the first end region is expandable to different angles relative to the longitudinal axis and maintained at the different angles upon release of the first force; and
a second end region coupled to the second end, the second end region configured to be delivered in the second heart chamber in a compressed delivery state and to transition to a deployed state therein, second selected portions of the second end region are configured to be independently, selectively deformable by a second force such that the second end region is expandable to different angles relative to the longitudinal axis and maintained at the different angles upon release of the second force,
wherein the first and second end regions are configured to anchor the middle region within a heart wall between the first heart chamber and the second heart chamber, and
wherein the different angles of the first and second end regions are selected to change a blood flow rate through the passage defined by the lumen to change a coefficient of discharge of the device.

2. The device of claim 1, wherein the first and second end regions comprise a plastically deformable material.

3. The device of claim 1, wherein the first and second end regions are configured to transition from the compressed delivery state to the deployed state via different sized non-compliant balloons.

4. The device of claim 1, wherein at least one of the selected portions of the first or second end regions are expandable to an angle between zero and 90 degrees relative to the longitudinal axis of the device.

5. The device of claim 1, wherein the first and second end regions comprise a plurality of support arms extending from the middle region, the plurality of support arms coupled circumferentially along outer edges of the middle region of the device.

6. The device of claim 1, wherein the first and second end regions are integrally formed with the middle region, the first and second end regions and the middle region comprising a plurality of longitudinal struts interconnected by a plurality of circumferential sinusoidal struts.

7. The device of claim 6, wherein at least one of the first or second end regions comprises at least one of a conical or bell shape.

8. The device of claim 1, wherein the middle region is configured to be adjusted from a first state having a first diameter to a second state having a second diameter different from the first diameter.

9. The device of claim 8, wherein the middle region comprises a plastically deformable material.

10. The device of claim 8, wherein the middle region comprises an expandable mesh tube.

11. The device of claim 8, wherein the second diameter is larger than the first diameter.

12. The device of claim 11, wherein the middle region is configured to be adjusted from the first state to the second state via an inflatable balloon catheter.

13. The device of claim 12, wherein the inflatable balloon catheter comprises a dog bone shape.

14. The device of claim 13, wherein the inflatable balloon catheter comprises a quadrilateral dog bone shape.

15. The device of claim 8, wherein the second diameter is smaller than the first diameter.

16. The device of claim 8, further comprising one or more sensors configured to measure blood flow through the passage between the first heart chamber and the second heart chamber, and wherein the middle region is configured to be adjusted from the first state to the second state responsive to the measured blood flow.

17. The device of claim 1, wherein the middle region of the device is further configured to be coupled to a medical device to thereby anchor the medical device within the heart wall between the first heart chamber and the second heart chamber.

18. The device of claim 17, wherein the medical device comprises at least one of an open atrial septal shunt, a valved atrial septal shunt, a left atrial blood pressure sensor, or a blood pump.

19. The device of claim 1, wherein the first heart chamber is a left atrium and the second heart chamber is a right atrium, and wherein the device is configured to permit blood flow through the passage between the left atrium and the right atrium.

20. A method for providing a passage between a first heart chamber and a second heart chamber, the method comprising:
selecting a device having a first end region, a second end region, and a middle region extending between the first and second end regions, the middle region having a lumen configured to provide the passage between the first heart chamber and the second heart chamber;
delivering the device in a compressed delivery state within a heart wall of a patient such that the first end region is disposed within the first heart chamber, the second end region is disposed within the second heart chamber, and the middle region is positioned within the heart wall;
expanding the first end region from the compressed delivery state to an expanded deployed state and independently, selectively deforming first selected portions of the first end region to different angles relative to a longitudinal axis of the device; and
expanding the second end region from the compressed delivery state to an expanded deployed state and independently, selectively deforming second selected portions of the second end region to different angles relative to a longitudinal axis of the device, thereby providing the passage through the lumen of the middle region between the first heart chamber and the second heart chamber,
wherein the different angles of the first and second end regions are selected to change a blood flow rate through the passage defined by the lumen to change a coefficient of discharge of the device.

21. The method of claim 20, further comprising adjusting an angle of the first end region relative to the longitudinal axis of the device, and adjusting an angle of the second end region relative to the longitudinal axis of the device to achieve a predetermined flowrate across the passage between the first heart chamber and the second heart chamber.

* * * * *